US007560425B2

(12) United States Patent
Brand et al.

(10) Patent No.: US 7,560,425 B2
(45) Date of Patent: Jul. 14, 2009

(54) PHARMACEUTICAL COMPOSITION CONSISTING OF RAPAMYCINE AND GASTRIN 17(LEU15) AND A METHOD FOR TREATING DIABETES

(75) Inventors: Stephen J. Brand, Lincoln, MA (US); Antonio Cruz, Toronto (CA)

(73) Assignee: Waratah Pharmaceuticals Inc., Toronto, Ontario (CA)

( * ) Notice: Subject to any disclaimer, the term of this patent is extended or adjusted under 35 U.S.C. 154(b) by 12 days.

(21) Appl. No.: 10/517,135

(22) PCT Filed: Jun. 9, 2003

(86) PCT No.: PCT/US03/18377

§ 371 (c)(1),
(2), (4) Date: Feb. 17, 2006

(87) PCT Pub. No.: WO03/103701

PCT Pub. Date: Dec. 18, 2003

(65) Prior Publication Data

US 2006/0183674 A1      Aug. 17, 2006

(51) Int. Cl.
A61K 38/00      (2006.01)
A01N 45/00      (2006.01)

(52) U.S. Cl. .......................... 514/2; 530/300; 530/309; 424/198.1; 524/26

(58) Field of Classification Search ....................... None
See application file for complete search history.

(56) References Cited

U.S. PATENT DOCUMENTS

| 5,624,895 | A | 4/1997 | Sobel | 514/8 |
|---|---|---|---|---|
| 5,885,956 | A | 3/1999 | Nardi et al. | 514/2 |
| 6,288,301 | B1 | 9/2001 | Nardi et al. | 800/18 |
| 6,558,952 | B1 | 5/2003 | Parikh et al. | 435/384 |
| 6,899,883 | B2 | 5/2005 | Dupre | 424/198.1 |
| 6,989,148 | B2 | 1/2006 | Dupre | 424/198.1 |
| 6,992,060 | B2 | 1/2006 | Brand | 514/2 |
| 7,037,504 | B2 | 5/2006 | Magil et al. | 242/198.1 |
| 2002/0081285 | A1 | 6/2002 | Parikh et al. | 424/93.21 |
| 2002/0119146 | A1 | 8/2002 | Dupre | 424/93.21 |
| 2003/0083259 | A1 | 5/2003 | Efendic et al. | 514/12 |
| 2003/0119734 | A1 | 6/2003 | Flink et al. | 514/12 |
| 2003/0224983 | A1 | 12/2003 | Nielsen | 514/12 |
| 2004/0023885 | A1 | 2/2004 | Brand et al. | 514/12 |
| 2004/0037818 | A1 | 2/2004 | Parikh et al. | 424/93.21 |
| 2004/0209801 | A1 | 10/2004 | Brand et al. | 514/12 |
| 2004/0209816 | A1 | 10/2004 | Parikh et al. | 514/12 |
| 2004/0229810 | A1 | 11/2004 | Cruz | 514/14 |
| 2004/0266682 | A1 | 12/2004 | Cruz | 514/12 |
| 2005/0222221 | A1 | 10/2005 | Demuth et al. | 514/365 |
| 2006/0189520 | A1 | 8/2006 | Brand et al. | 514/12 |
| 2006/0234373 | A1 | 10/2006 | Rabinovitch et al. | 435/325 |
| 2006/0234932 | A1 | 10/2006 | Brand | 514/12 |

FOREIGN PATENT DOCUMENTS

| EP | 0 507 555 B1 | 10/1992 |
|---|---|---|
| WO | WO 95/19785 | 7/1995 |
| WO | WO 95/31214 | 11/1995 |
| WO | WO 00/44400 | 8/2000 |
| WO | WO 02/12452 A2 | 2/2002 |
| WO | WO 02/055152 A2 | 7/2002 |
| WO | WO 03/040310 A2 | 5/2003 |
| WO | WO 03/100024 A2 | 12/2003 |
| WO | WO 03/103701 A1 | 12/2003 |
| WO | WO 2004/037195 A2 | 5/2004 |
| WO | WO 2004/045640 A1 | 6/2004 |
| WO | WO 2004/096853 A1 | 11/2004 |
| WO | WO 2004/105780 A2 | 12/2004 |
| WO | WO 2005/072045 A2 | 8/2005 |
| WO | WO 2006/002532 A1 | 1/2006 |
| WO | WO 2007/041833 A1 | 4/2007 |
| WO | WO 2007/062531 A1 | 6/2007 |
| WO | WO 2007/095737 A1 | 8/2007 |

OTHER PUBLICATIONS

Carpenter, et al., "The Epidermal Growth Factor Family", *Eds. Sporn and Roberts*, Chapter 4:69-171 (1990).

Fridkis-Hareli, et al., "Novel Synthetic Amino Acid Copolymers that Inhibit Autoantigen-Specific T Cell Responses and Suppress Experimental Autoimmune Encephalomyelitis", *J. Clin. Invest.*, 109(12):1635-1643 (2002).

Lin, et al., "A71378: a CCK Agonist with High Potency and Selectivity for CCK-A Receptors", *Am. J. Physiol.*, 258(4 Pt 1):G648-G651 (1990).

Rooman, et al., "Gastrin Stimulates β-Cell Neogenesis and Increases Islet Mass From Transdifferentiated but not from Normal Exocrine Pancreas Tissue", *Diabetes*, 51(3):686-690 (2002).

(Continued)

*Primary Examiner*—Robert Landsman
*Assistant Examiner*—Gyan Chandra
(74) *Attorney, Agent, or Firm*—Ivor R. Elrifi; David E. Johnson; Mintz Levin Cohn Ferris Glovsky and Popeo PC

(57) ABSTRACT

Compositions and methods for islet neogenesis therapy comprising an EGF and a gastrin in combination with immune suppression, and for treating or preventing early stage diabetes with a gastrin/CCK receptor ligand and an immunosuppressant are provided.

9 Claims, 4 Drawing Sheets

OTHER PUBLICATIONS

Sasaki, et al., "Dietary Docosahexaenoic Acid Can Alter the Surface Expression of CD4 and CD8 on T Cells in Peripheral Blood", *J. Agric. Food Chem.*, 48(4):1047-1049 (2000).

Selinfreund, et al., "Antisense Inhibition of Glial S100β Production Results in Alterations in Cell Morphology, Cytoskeletal Organization, and Cell Proliferation", *J. Cell. Biol.*, 111:2021-2028 (1990).

Vergelli, et al., "Immunosuppressive Activity of 13-cis-Retinoic Acid in Rats: Aspects of Pharmacokinetics and Pharmacodynamics", *Immunopharmacology*, 37:191-197 (1997).

Winer, et al., "Autoimmune Islet Destruction in Spontaneous Type 1 Diabetes is not β-Cell Exclusive", *Nature Medicine*, 9(2):198-205 (2003).

Adams et al., "Insulin-like growth factor-I promotes successful fetal pancreas transplantation in the intramuscular site", *Surgery*, 116:751-757 (1994).

Ahmed et al., "High and Low Affinity Receptors Mediate Growth Effects of Gastrin and Gastrin-Gly on DLD-1 Human Colonic Carcinoma Cells", *FEBS Letters*, 556:199-203 (2004).

Aly et al., "Short-term infusion of glycine-extended gastrin$_{17}$ stimulates both proliferation and formation of aberrant crypt foci in rat colonic mucosa", *International Journal Cancer*, 94:307-313 (2001).

Aly et al., "Gastrins, cholecystokinins and gastrointestinal cancer", *Biochimica et Biophysica Acta*, 1704:1-10 (2004).

Araki et al., "Stability of Recombinant Epidermal Growth Factor in Various Solutions", *Chem. Pharm. Bull.*, 37(2):404-406 (1989).

Baggio et al., "Sustained Expression of Exendin-4 Does Not Perturb Glucose Homeostasis, b-Cell Mass, or Food Intake in Metallothionein-Preproexendin Transgenic Mice", *J Biol Chem*, 275:34472-34477 (2000).

Baggio et al., "Therapeutic approaches to preserve islet mass in type 2 diabetes", *Annual Review of Medicine*, 57:265-281 (2006).

Baldwin, G.S., "The role of gastrin and cholecystokinin in normal andneoplastic gastrointestinal growth", *J. Gastroenterol. Hepatol.*, 10(2):215-232 (1995).

Baldwin et al., "Measurement of Gastrin and Transforming Growth Factor α Messenger RNA Levels in Colonic Carcinoma Cell Lines by Quantitative Polymerase Chain Reaction", *Cancer Research*, 52:2261-2267 (1992).

Beger et al., "RS-61443 Prevents Microvascular Rejection of Pancreatic Islet Xenografts", *Transplantation*, 63(4):577-582 (1997).

Berendsen, H.J.C., "A glimpse of the Holy Grail?", *Science*, 282:642-643 (1998).

Bonato et al., "Guinea Pig 33-Amino Acid Gastrin", *Life Science*, 39:959-964 (1986).

Boniface et al., "Clearance Rate, Half-Life, and Secretory Potency of Human Gastrin-17-I in Different Species", *Gastroenterology*, 71(2):291-294 (1976).

Bosch et al., " Epidermal Growth Factor Mimics Insulin Effects in Rat Hepatocytes", *Biochem J*, 239:523-530 (1986).

Bower et al., "The inhibition of gastric acid secretion by epidermal growth factor", *Experientia*, 31(7):825-826 (1975).

Brand et al., "Differential Gastrin Gene Expression in Rat Gastrointestinal Tract and Pancreas during Neonatal Development", *J. Biol. Chem*, 263(11):5341-5347 (1988).

Brand et al., "Gastrin Gene Expression and Regulation in Rat Islet Cell Lines", *J. Biol. Chem*, 263:16597-16603 (1994).

Brand et al., "Pharmacological Treatment of Chronic Diabetes by Stimulating Pancreatic b-Cell Regeneration with Systemic Co-administration of EGF and Gastrin", *Pharmacology & Toxicology*, 91(6):414-420 (2002).

Brand et al., "Prolonged Efficacy of Islet Neogenesis Therapy with Gastrin and TGFα in Mature Rats with Preexisting Diabetes", *Diabetes*, 50(Suppl 2):A338 (Abstract) (2001).

Brenna et al., "Trophic effect of gastrin on the enterochromaffin like cells of the ratstomach: establishment of a dose response relationship", *Gut*, 33(10):1303-1306 (1992).

Burgess et al., "Murine Epidermal Growth Factor: Structure and Function", *Biochemistry*, 27:4977-4985 (1988).

Burgess et al., "Two Forms of Murine Epidermal Growth Factor: Rapid Separation by Using Reverse-Phase HPLC", *Proc. Natl. Acad. Sci. U.S.A.*, 79:5753-5757 (1982).

Calnan et al., "Potency and Stability of C Terminal Truncated Human Epidermal Growth Factor", *Gut*, 47:622-627 (2000).

Campbell et al., "Structure-function relationships in epidermal growth factor (EGF) and transforming growth factor-alpha (TGF-alpha)", *Biochem. Pharmacol.*, 40:35-40 (1990).

Carlsson et al., "Gastrin and gastric enterochromaffin-like cell carcinoids in the rat", *Digestion*, 47(Suppl 1):17-23, "Discussion", pp. 49-52 (1990).

Carpenter et al., "Human Epidermal Growth Factor and the Proliferation of Human Fibroblasts", *J. Cell Physiol*, 88:227-237 (1976).

Carver et al., "A high resolution 1H NMR study of the solution structure of human epidermal growth factor", *FEBS Lett.*, 205(1):77-81 (1986).

Chatenoud, L., "Restoration of Self-Tolerance Is a Feasible Approach to Control Ongoing Beta-Cell Specific Autoreactivity: Its Relevance for Treatment in Established Diabetes and Islet Transplantation", *Diabetologia*, 44:521-536 (2001).

Chatenoud et al., "Anti-CD3 Antibody Induces Long-Term Remission of Overt Autoimmunity in Nonobese Diabetic Mice", *Proc Natl Acad Sci U S A*, 91:123-127 (1994).

Chen et al., "Time course of hypertrophic and ultrastructural responses of rat stomach enterochromaffin-like cells to sustained hypergastrinemia", *Cell Tissue Res*, 284(1):55-63 (1994).

Clare et al., "Production of Mouse Growth Factor in Yeast: High-Level Secretion Using *Pichia pastoris* Strains Containing Multiple Gene Copies", *Gene*, 105:205-212 (1991).

Conteas et al., "The Effects of Gastrin, Epidermal Growth Factor, and Somatostatin on DNA Synthesis in a Small Intestinal Crypt Cell Line (IEG-6) (42484)", *Proc. Soc. Exp. Biol. Med.*, 184(3):307-311 (1987).

Cooke et al., "The solution structure of human epidermal growth factor", *Nature*, 327:339-341 (1987).

Cras-Meneur et al., "Epidermal growth factor increases undifferentiated pancreatic embryonic cells in vitro: a balance between proliferation and differentiation", *Diabetes*, 50:1571-1579 (2001).

Crean et al., "Parietal cell hyperplasia induced by the administration of pentagastrin (ICI 50,123) to rats", *Gastroenterology*, 57(2):147-155 (1969).

Creutzfeldt et al., "Is hypergastrinaemia dangerous to man?", *Scand J Gastroenterol Suppl.*, 180:179-191 (1991).

Database GenCore on EST, ID AAP61038, Billing-Medel et al., "Reagants and methods useful for detecting diseases of the breast", *Gene Sequence* (2003).

Database GenCore on EST, ID 152995, Saggi et al., "Cloning and Sequencing of the Rat Preproepidermal Growth Fact cDNA", *Gene Sequence* (2003).

Datta et al., "Ionizing radiation activates transcription of the EGRI gene via CArG elements", *Proc. Natl. Acad. Sci. USA*, 89:10149-10153 (1992).

Dembinski et al., "Trophic Action of Epidermal Growth Factor on the Pancreas and Gastroduodenal Mucosa in Rats", *J Physiol (Lond)*, 325:35-42 (1982).

Dembinski et al., "Stimulation of Pancreatic Growth by Secretin, Caerulein, and Pentagastrin", *Endocrinology*, 106(1):323-328 (1980).

Di Lorenzo et al., "Involvement of growth factor receptors of the epidermal growth factor receptor family in prostate cancer development and progression to androgen independence", *Clin. Prostate Cancer*, 2(1):50-57 (2003).

DiAugustine et al., "Evidence for Isoaspartyl (Deamidated) Forms of Mouse Epidemal Growth Factor", *Analytical Biochemistry*, 165:420-429 (1987).

Dockray, G.J., "Gastrin", *Best Practice & Research Clinical Endocrinology & Metabolism*, 18(4):555-568 (2004).

Dockray, G.J., "Gastrin and gastric epithelial physiology", *J Physiol.*, 518(Pt. 2):315-324(1999).

Dockray et al., "Immunochemical Characterization of Gastrin in Pancreatic Islets of Normal and Genetically Obese Mice", *J Endocrinol*, 72:143-151(1977).

Dockray et al., "Postsecretory Processing of Heptadecapeptide Gastrin: Conversion to C- Terminal Immunoreactive Fragments in the Circulation of the Dog", *Gastroenterology*, 83:224-232 (1982).

Drumm et al., "Urogastrone/epidermal growth factor in treatment of congenital microvillous atrophy", *Lancet*, 1(8577):111-112 (1988).

Dupre et al., "Affects of Secretin, Pancreozymin, or Gastrin on the Response of the Endocrine Pancreas to Administration of Glucose or Arginine in Man", *Journal of Clinical Investigation* 48:745-757 (1969).

Durrant et al., "Co-stimulation of Gastrointestinal Tumour Cell Growth by Gastrin, Transforming Growth Factor α and Insulin Like Growth Factor-1", *Brit. J. Cancer*, 63:67-70 (1991).

Efrat, S., "Prospects for gene therapy of insulin-dependent diabetes mellitus", *Diabetologia*, 41:1401-1409 (1998).

Elder et al., "Effect of urogastrone on gastric secretion and plasma gastrin levels in normal subjects", *Gut*, 16(11):887-893 (1975).

Elder et al., "Effect of urogastrone in the Zollinger-Ellison syndrome", *The Lancet*, 2(7932):424-427 (1975).

Ennis et al., "The EGF receptor system as a target for antitumor therapy", *Cancer Invest.*, 9(5):553-562 (1991).

Ferrara et al., "Molecular and Biological Properties of the Vascular Endothelial Growth Factor Family of Proteins", *Endocr Rev*, 13(1):18-32 (1992).

Gasslander et al., "Trophic Effects by Epidermal Growth Factor on Duodenal Mucosa and Exocrine Pancreas in Rats", *Eur Surg Res*, 29:142-149 (1997).

George-Nascimento et al., "Characterization of Recombinant Human Epidermal Growth Factor Produced in Yeast", *Biochemistry*, 27:797-802 (1988).

George-Nascimento et al., "Replacement of a Labile Aspartyl Residue Increases the Stability of Human Epidermal Growth Factor", *Biochemistry*, 29:9584-9591 (1990).

Goodlad et al., "Comparison of the Mitogenic Activity of Human Epidermal Growth Factor 1-53 and Epidermal Growth Factor I-48 in vitro and in vivo", *Clinical Sciences*, 91:503-507 (1996).

Goodlad et al., "Intravenous but not intragastric urogastrone-EGF is trophic to the intestine of parenterally fed rats", *Gut*, 28:573-582 (1987).

Guglietta et al., "Effect of h-EGF and h-EGF 1-48 on histamine-stimulated gastric acid secretion in rats and monkeys", *J. Physiol Paris*, 87:343-347 (1993).

Guglietta et al., "Clinical applications of epidermal growth factor", *Eur. J. Gastroenterol. Hepatol.*, 7(10):945-950 (1993).

Hakanson et al., "Hypergastrinaemia produces trophic effects in stomach but not in pancreas and intestines", *Regul. Pept.*, 13:225-233 (1986).

Hayashi et al., "A Sensitive Enzyme Immunoassay for Human Epidermal Growth Factor. Determination of HEGF in Human Serum and Urine and Pharmacokinetics in Mouse", *J Pharmacobiodyn*, 12:410-415 (1989).

Hayek et al., "Growth Factor/Matrix-Induced Proliferation of Human Adult Beta-Cells", *Diabetes*, 44:1458-1460 (1995).

Heath et al., "A synthetic approach to structure-function relationships in the murine epidermal growth factor molecule", *Proc. Natl. Acad. Sci, U.S.A.*, 83:6367-6371 (1986).

Herbst, R.S., "Review of epidermal growth factor receptor biology", *Int. J. Radiat. Oncol. Biol. Phys.*, 59(2 Suppl.):21-26 (2004).

Herbst et al., "Epidermal growth factor receptors as a target for cancer treatment: the emerging role of IMC-C225 in the treatment of lung and head and neck cancers", *Semin. Oncol.*, 29(1, Suppl. 4):27-36 (2002).

Herold et al., "Prevention of Autoimmune Diabetes With Nonactivating Anti-CD3 Monoclonal Antibody", *Diabetes*, 41:385-391(1992).

Herold et al., "Anti-CD3 Monoclonal Antibody in New-Onset Type 1 Diabetes Mellitus", *N Engl J Med*, 346(22):1692-1698 (2002).

Herold et al., "A Single course of Anti-CD3 Monoclonal Antibody hOKT3yl(Ala-Ala) Results in Improvement in C-Peptide Responses and Clinical Parameter for at Least 2 years after Onset of Type 1 Diabetes", *Diabetes*, 54:1763-1769 (2005).

Hollande et al., "In Vitro Secretion of Gastrin, Insulin, and Glucagon in Tissue Cultures of Pancreas From a Child with Neonatal Intractable Hypoglycemia", *Gastroenterology*, 71(2):255-262 (1976).

Hollenberg et al., "Epidermal Growth Factor-Urogastone: Biological Activity and Receptor Binding of Derivatives", *Molecular Pharmacology*, 17:314-320 (1980).

Ito et al., "Structural analysis of the gene encoding human gastrin: The large intron contains an *Alu* sequence", *Proc. Natl. Acad. Sci. USA*, 81(15):4662-4666 (1984).

Jensen, R., "Gastrinoma as a model for prolonged hypergastrinemia in the human", in *Gastrin*, Chapter 29, pp. 373-393, Raven Press Ltd., New York (1993).

Juhl et al., "Systemic Treatment With Recombinant Human Epidermal Growth Factor Accelerates Healing of Sclerotherapy-Induced Esophageal Ulcers and Prevents Esophageal Stricture Formations in Pigs", *Dig Dis Sci*, 39:2671-2678 (1994).

Karnes, Jr., W.E., "Epidermal Growth Factor and Transforming Growth Factor-alpha", in *Gut Peptides: Biochemistry and Physiology*, Chapter 20, pp. 553-586, Raven Press Ltd., New York (1994).

Keiser et al., "Hemodynamic effects of epidermal growth factor in conscious rats and monkeys", *Proc. Natl. Acad. Sci. U.S.A*, 93:4957-4961 (1996).

Keymeulen et al., "Insulin Needs After CD3-Antibody Therapy in New-Onset Type 1 Diabetes", *New England Journal of Medicine*, 352:2598-2608 (2005).

Kim et al., "EGF receptor signaling in prostate morphogenesis and tumorigenesis", *Histol. Histopathol.*, 14(4):1175-1182 (1999).

Koch et al., "Molecular Species of Epidermal Growth Factor Carrying Immunosuppressive Activity", *Journal of Cellular Biochemistry*, 25:45-59 (1984).

Koffman et al., "Effect of urogastrone on gastric secretion and serum gastrin concentration in patients with duodenal ulceration", *Gut*, 23(11):951-956 (1982).

Konturek et al., "Release and action of epidermal growth factor on gastric secretion in humans", *Scand. J. Gastroenterol.*, 24(4):485-492 (1989).

Konturek et al., "Comparison of Organ Uptake and Disappearance Half-Time of Human Epidermal Growth Factor and Insulin", *Regul Pept*, 30:137-146 (1990).

Kopin et al., "The role of the cholecystokinin-B/gastrin receptor transmembrane domains in determining affinity for subtype-selective ligands", *J Biol Chem*, 270(10):5019-5023 (1995).

Korc et al., "Regulation of Protein Synthesis in Normal and Diabetic Rat Pancreas by Cholecystokinin", *Am J Physiol*, 241:G116-G121 (1981).

Korc, M.J., "Islet Growth Factors: Curing Diabetes and Preventing Chronic Pancreatis?", *Clin. Invest.*, 92:1113-1114 (1993).

Kuo et al., "Pharmacokinetic Evaluation of Two Human Epidermal Growth Factors (hEGF51 and hEGF53) in Rats", *Drug Metabolism and Description*, 20(1):23-30 (1991).

Larsson et al., "Pancreatic gastrin in foetal and neonatal rats", *Nature*, 262:609-610 (1976).

Lima-Leite et al., "Synthesis and Biological Activities of the Human Gastrin analogs", *Brazilian Journal of Medical and Biological Research*, 29(10):1253-1263 (1996).

Marti et al., "Biological effects of epidermal growth factor, with emphasis on the gastrointestinal tract and liver: an update", *Hepatology*, 9(1):126-138 (1989).

Martindale: The Extra Pharmacopoeia, 13th Edition, The Pharmaceutical Press, London, pp. 869-898 (1993).

Maton et al., "Long-Term Efficacy and Safety of Omeprazole in Patients With Zollinger- Ellison Syndrome: a Prospective Study", *Gastroenterology*, 97:827-836 (1989).

Merchant et al., "Epidermal Growth Factor Stimulation of the Human Gastrin Promoter Requires Sp1", *J Biol Chem*, 270(11):6314-6319 (1995).

Merlino, G., "Epidermal growth factor receptor regulation and function", *Semin. Cancer Biol.*, 1:277-284 (1990).

Morley et al., "Structure-Function Relationships in the Active C-Terminal Tetrapeptide Sequence of Gastrin", *Nature*, 207:1356-1359 (1965).

Morley, J.S., "Synthesis of Hunam Gastrin(I) and the Biological Properties of Analogues", in *Peptides*, pp. 226-234, North Holland Publishing Co., Amersterdam (1967).

Morley et al., "Polypeptides. Part IX. Variations of the Methionyl Position in the C-terminal Tetrapeptide Amide Sequence of the Gastrins", *J. Chem, Soc.*, 726-733 (1968).

Mottram et al., "Remission and Pancreas Isograft Survival in Recent Onset Diabetes NOD Mice After Treatment with Low-Dose Anti-CD3 Monoclonal Antibodies", *Transplant Immunology*, 10:63-72 (2002).

Normanno et al., "EGF-related peptides in the pathophysiology of the mammary gland",*J. Mammary Gland Biol. Neoplasia*, 2(2):143-151 (1997).

Ohlsson et al., "The Method of Administration of Cholecystokinin Determines the Effects Evoked in the Pancreas", Pancreas, 23(1):94-101 (2001).

Ohlsson et al., "The Effect of Intermittent Injections of CCK-8S and the CCK-A Receptor Antagonist Devazepide on Cell Proliferation in Exocrine Rat Pancreas", *Int J Pancreatol*, 24(3):211-218 (1998).

Ohlsson et al., "Epidermal Growth Factor Induces Cell Proliferation in Mouse Pancreas and Salivary Glands", *Pancreas*, 14(1):94-98 (1997).

Orbuch et al., "Prolonged hypergastrinemia does not increase the frequency of colonic neoplasia in patients with Zollinger-Ellison syndrome", *Dig. Dis. Sci.*, 41(3):604-613 (1996).

Orkin et al., "Report and Recommendations of the Panel to Assess the NIH Investment in Research on Gene Therapy" (Dec. 7, 1995).

Patel et al., "Treatment of non-insulin-dependent diabetes mellitus", *Expert Opinion Investig Drugs*, 12(4):623-633 (2003).

Pauwels et al., "Metabolism of Heptadecapeptide Gastrin in Humans Studied by Region-specific Antisera", *J. Clin. Invest.*, 75:2006-2013 (1985).

Pearson, W.R., "Empirical Statistical Estimates for Sequence Similarity Searches",*J. Mol. Biol.*, 276:71-84 (1998).

Pederson et al., "Effect of Cholecystokinin, Secretin, and Gastric Inhibitory Polypeptide on Insulin Release From the Isolated Perfused Rat Pancreas", *Can J Physiol Pharmacol*, 57:1233-1237 (1979).

Pratha et al., "Inhibition of pentagastrin-stimulated gastric acid secretion by pantoprazole and omeprazole in healthy adults", *Digestive Diseases and Sciences*, 51(1):123-131 (2006).

Rehfeld et al., "The Effect of Gastrin on Basal- and Glucose-Stimulated Insulin Secretion in Man", *J Clin Invest*, 52:1415-1426 (1973).

Rehfeld et al., "The Effect of Gastrin and Cholecystokinin on the Endocrine Pancreas", *Frontiers of Hormone Research*, 7:107-118 (1980).

Reilly, J., "Safety profile of the proton-pump inhibitors", *Am. J. Health Syst. Pharm.* 1:56(23 Suppl 4): S11-S17 (1999).

Robinson et al., "The international standard for epidermal growth factor (EGF): Comparison of candidate preparations by in vitro bioassays and immunoassays",*Growth Factors*, 13:163-170 (1996).

Rooman et al., "Mitogenic effect of gastrin and expression of gastrin receptors in duct-like cells of rat pancreas", *Gastroenterology*, 121:940-949 (2001).

Rooman et al., "Effects of gastrin on proliferating and differentiation in regenerating pancreas", *Diabetologia*, pp. 106 (Abstract) (2000).

Rooth et al., "Prevention of detrimental effect of cyclosporin A on vascular ingrowth of transplanted pancreatic islets with verapamil", *Diabetes*, 38(Suppl. 1):202-205 (1989).

Rozengurt et al., "Gastrin, CCK, signaling, and cancer",*Annu. Rev. Physiol.*, 63:49-76 (2001).

Ryberg et al., "Trophic Effects of Continuous Infusion of [Leu$^{15}$]-Gastrin-17 in the Rat", *Gastroenterology*, 98(1):33-38 (1990).

Schally et al., "New approaches to therapy of cancers of the stomach, colon and pancreas based on peptide analogs", *Cell. Mol. Life Sci.*, 61(9):1042-1068 (2004).

Scheving et al., "Circadian phase-dependent stimulatory effects of epidermal growth factor on deoxyribonucleic acid synthesis in the tongue, esophagus, and stomach of the adult male mouse", Endocrinology, 105:1475-1480 (1979).

Seva et al., "Growth-Promoting Effects of Glycine-Extended Progastrin", *Science*, 265:410-412 (1994).

Shapiro et al., "Combination Therapy With Low Dose Sirolimus and Tacrolimus Is Synergistic in Preventing Spontaneous and Recurrent Autoimmune Diabetes in Non-Obese Diabetic Mice", *Diabetologia*, 45:224-230 (2002).

Shapiro et al., "Islet Transplantation in Seven Patients with Type 1 Diabetes Mellitus using a Glucocorticoid-Free Immunosuppressive Regimen",*New England Journal of Medicine*, 343(4):230-238 (2000).

Shin et al., "Synthesis and Biological Activity of N-Terminal-Truncated Derivatives of Human Epidermal Growth Factor (h-EGF)", *Peptides*, 16(2):205-210 (1995).

Simpson et al., "Rat epidermal growth factor: complete amino acid sequence",*Eur. J. Biochem.*, 153:629-637 (1985).

Singh et al., "Novel Gastrin Receptors Mediate Mitogenic Effects of Gastrin and Processing Intermediates of Gastrin on Swiss 3T3 Fibroblasts", *J. Biol. Chem*, 270(15):8429-8438 (1995).

Sinha et al., "Epidermal growth factor enemas are effective in the treatment of left-sided ulcerative colitis", *AGA*, (Abstract) (2001).

Sizemore et al., "Impact of Receptor Downregualtion on Clearance of Two Human EGFs With Different Receptor Binding Activity", *Peptides*, 17(7):1229-1236 (1996).

Slice et al., "Gastrin and EGF Synergistically Induce Cyclooxygenase2 Expression in Swiss 3T3 Fibroblasts that Express the $CCK_2$ Receptor", *J. Cellular Physiology*, 196:454-463 (2003).

Slover et al., "Prevention of Type I Diabetes and Recurrent Beta-Cell Destruction of Transplanted Islets", *Endocr Rev*, 18(2):241-258 (1997).

Soon-Shiong et al., "Long-term reversal of diabetes by the injection of immunoprotected islets", *Proc. Natl. Acad. Sci USA*, 90(12):5843-5847 (1993).

Stadil et al., "Preparation of $^{125}$I-Labelled Synethic Human Gastrin I for Radioimmunoanalysis", *Scand J Clin Lab Invest*, 30:361-368 (1972).

Stagsted et al., "Insulinomimetic effect on glucose transport by epidermal growth factor when combined with a major histocompatibility complex class I-derived peptide",*J. Biol. Chem.*, 268(3):1770-1774 (1993).

Suarez-Pinzon et al., "Combination Therapy with Epidermal Growth Factor and Gastrin Increases Beta-Cell Mass and Reverses Hyperglycemia in Diabetic NOD Mice", *Diabetes*, 54:2596-2601 (2005).

Suarez-Pinzon et al., "Combination therapy with epidermal growth factor and gastrin induces neogenesis of human islet beta cells from pancreatic duct cells and an increase in functional beta-cell mass", *J Clin Endocrinol & Metabolism*, 90(6):3401-3409 (2005).

Sullivan et al., "Epidermal growth factor in necrotizing enteritis [letter]", *The Lancet*, 338(8758):53-54 (1991).

Svoboda et al., "Structural characterization and biological activity of recombinant human epidermal growth factor proteins with different N-terminal sequences", *Biochimica et Biophysica Acta*, 1206:35-41 (1994).

Taylor et al., "Effect of individual L-amino acids on gastric acid secretion and serum gastrin and pancreatic polypeptide release in humans", *Gastroenterology*, 83:273-278 (1982).

Taylor et al., "Serum gastrin in patients with chronic renal failure", *Gut*, 21(12):1062-1067 (1980).

Thomas et al., "Role of gastrointestinal hormones in the proliferation of normaland neoplastic tissues", *Endocr. Rev.*, 24(5);571-599 (2003).

Tracy et al., "Physiological Properties of a Series of Synthetic Peptides Structurally Related to Gastrin 1", *Nature*, 204:935-938 (1964).

"Transition Therapeutics Confirms Effectiveness of Islet Neogenesis Therapy in Reducing Diabetic Symptoms", Transition Therapeutics Press Release, Apr. 17, 2002.

"Transition Therapeutics Inc. Receives Approval to Initiate Phase I Clinical Trial for Islet Neogenesis Therapy", Transition Therapeutics Press Release, Sep. 20, 2002.

"Transition Therapeutics' I.N.T.™ Treatment Stimulates Regeneration of Human Insulin-Producing Cells", Transition Therapeutics Press Release, Sep. 26, 2002.

"Transition Therapeutics' I.N.T.™ Treatment Increases Survival" , Transition Therapeutics Press Release, Sep. 27, 2002.

Unger et al., "The Effects of Secretin, Pancreozymin, and Gastrin on Insulin and Glucagon Secretion in Anethetized Dogs", *Journal of Clinical Investigation*, 46(4);630-645 (1967).

Vinter-Jensen, L., "Pharmacological Effects of Epidermal Growth Factor (EGF) with focus on the urinary and gastrotestinal tracts", *APMIS*, 107(Suppl. 93):1-42 (1999).

Vinter-Jensen et al., "Systemic Treatment with Epidermal Growth Factor in Pigs Induces Ductal Proliferations in the Pancreas", *Gastroenterology*, 113:1367-1374 (1997).

Walker-Smith et al., "Intravenous epidermal growth factor/urogastrone increases small-intestinal cell proliferation in congenital microvillous atrophy", *The Lancet*, 2(8466):1239-1240 (1985).

Wallmark et al., "The Relationship Between Gastric Acid Secretion and Gastric $H^+$, $K^+$-ATPase Activity", *J. Biol. Chem.*, 260(25):13681-13684 (1985).

Walsh et al., "pH dependence of acid secretion and gastrin release in normal and ulcer subjects", *J. Clin. Invest*, 55:462-468 (1975).

Walsh, J., "Gastrin", in *Gut Peptides: Biochemistry and Physiology*, Chapter 4, pp. 75-121, Raven Press Ltd., New York (1994).

Wang et al., "Intraportal delivery of immunosuppression to intrahepatic islet allograft recipients", *Transp. Int.*, 8:268-272 (1995).

Wang et al., "Pancreatic duct cells express gastrin and TGF-alpha during duct to islet-cell differentiation in duct-ligated adult rats", *Diabetologia*, 39(Supplement 1):A63 (Abstract) (1996).

Wang et al., "Expression of gastrin and transforming growth factor-α during duct to islet cell differentiation in the pancreas of duct-ligated adult rats", *Diabetologia*, 40:887-893 (1997).

Wang et al, "Function and Regulation of Gastrin in Transgenic Mice: A Review", *Yale Journal of Biology and Medicine*, 65:705-713 (1992).

Wank, S.A., "Cholecystokinin Receptors", *Am J Physiol*, 269:G628-G646 (1995).

Wank et al, "Cholecystokinin Receptor Family. Molecular Cloning, Structure, and Functional Expression in Rat, Guinea Pig, and Human", *Ann N Y Acad Sci*, 713:49-66 (1994).

Wennberg et al., "Efficacy of Immunosuppressive Drugs in Islet Xenotransplantation", *Transplantation*, 63(9);1234-1242 (1997).

Wiborg, O., "Structure of a Human Gastrin Gene", *Proc Natl Acad Sci USA*, 81:1067-1069 (1984).

Yamaoka et al., "Development of Pancreatic Islets (Review)", *International Journal of Molecular Medicine*, 3(3):247-261 (1999).

Yano et al., "Effects of Intrahepatic Arterial and Intraportal Administration of FK506 on Liver Allograft Survival in Rats", *Transpl. Int.*, 7(Suppl. 1):S187-S193 (1994).

PHARMACEUTICAL COMPOSITION CONSISTING OF RAPAMYCINE AND GASTRIN 17(LEU15) AND A METHOD FOR TREATING DIABETES

FIELD OF THE INVENTION

The invention relates to methods and compositions for treating a diabetic subject with islet neogenesis therapy (I.N.T.™) and an agent for immunosuppression, and with a gastrin/CCK ligand receptor and an agent for immunosuppression.

BACKGROUND OF THE INVENTION

About 800,000 people in the United States population suffer from insulin deficiency diabetes (also known as juvenile or type I diabetes), and about 30,000 new cases arise each year. Further, an extremely large and rapidly increasing number of patients have forms of type II diabetes (also called adult onset or insulin-resistance diabetes), in this population at a level of epidemic proportions that cause pancreatic exhaustion and insulin insufficiency.

The abnormally high blood glucose (hyperglycemia) that characterizes diabetes, if left untreated, results in a variety of pathological conditions, for example, non-healing peripheral vascular ulcers, retinal damage leading to blindness, and kidney failure. Diabetes of both types I and II are treated with insulin injection in response to blood glucose levels determined by patient glucose self-monitoring, although not all type II patients progress to requiring insulin therapy. Typically, multiple doses of insulin are delivered by the patient per day. Severe pathological consequences of diabetes are correlated with less rigorous control of blood glucose level.

SUMMARY OF EMBODIMENTS

In one aspect, an embodiment of the invention is a method for manufacture of a medicament for use in treating a diabetic subject, the method comprising administering to the subject a composition for islet neogenesis therapy and an agent for suppressing an immune response. The method further uses a composition for islet neogenesis therapy that comprises an EGF receptor ligand. The method further uses a composition for islet neogenesis therapy that comprises at least two agents for suppressing an immune response. The composition of the method for islet neogenesis therapy comprises a gastrin/cholecystekinin (CCK) receptor ligand. The EGF receptor ligand is a recombinant human EGF, for example, the EGF receptor ligand is EGF51N. The gastrin/CCK receptor ligand is human gastrin17. In related embodiments, the agent for suppressing immune response is a drug, for example, the agent for suppressing immune response is at least one selected from of the group consisting of a rapamycin; a corticosteroid; an azathioprine; mycophenolate mofetil; a cyclosporine; a cyclophosphamide; a methotrexate; a 6-mercaptopurine; FK506 (Tacrolimus); 15-deoxyspergualin; an FTY 720; a mitoxantrone; a 2-amino-1,3-propanediol; a 2-amino-2[2-(4-octylphenyl)ethyl]propane-1,3-diol hydrochloride; a 6-(3-dimethyl-aminopropionyl) forskolin; and a demethimmunomycin. The rapamycin is Everolimus or Sirolimus. The corticosteroid is dexamethasone. The agent for suppressing immune response is a protein, for example, the protein comprises an amino acid sequence of an antibody. Exemplary antibodies for suppressing immune response can be at least one selected from the group consisting of: huI 124; BTI-322; allotrap-HLA-B270; OKT4A; Enlimomab; ABX-CBL; OKT3; ATGAM; basiliximab; daclizumab; antithymocyte immunoglobulin; ISAtx247; Medi-500; Medi-507; Alefacept; efalizumab; infliximab; in an alternative embodiment, the protein is a cytokine or growth factor such as GFAP, S100β, or an interferon.

According to these methods, the islet neogenesis therapy composition and the agent for suppressing immune response are formulated for sequential administration. One example comprises formulating the islet neogenesis therapy composition and the agent for suppressing immune response for sequential administration, and for allowing a period of time of at least one day between administering the agent and administering the composition. Alternatively, the period is at least one week, or at least six weeks between administering the agent and administering the composition.

In the above embodiments, at least one of the islet neogenesis therapy composition and the agent for suppressing immune response is formulated for systemic administration. Alternatively, at least one of the islet neogenesis therapy composition and the agent for suppressing immune response is formulated for bolus administration. For example, at least one of the islet neogenesis therapy composition and the agent for suppressing immune response is formulated for administration by a route selected from the group consisting of intravenous, subcutaneous, intraperitoneal, and intramuscular. In certain embodiments, the agent for suppressing immune response is formulated for oral administration. In certain embodiments, the agent for suppressing immune response is at least one selected from the group of Sirolimus, Tacrolimus, Everolimus, ISAtx247, and daclizumab.

In most cases, the subject for which the use is formulated is a diabetic mammal, for example, the subject is a human. Alternatively, the subject can be an experimental animal, for example, an NOD mouse.

In another aspect, an embodiment of the invention is a method for manufacture of a medicament for use in treating a diabetic subject, the method comprising formulating for the subject a composition for islet neogenesis therapy consisting of at least one of an EGF receptor ligand and a gastrin/CCK receptor ligand, and administering at least one immunosuppressing agent. In a related embodiment, the method involves further formulating the gastrin/CCK receptor ligand and the at least one immunosuppressing agent in the absence of the EGF receptor ligand. In one embodiment of the method, prior to further administering the gastrin/CCK receptor ligand and the at least one immunosuppressing agent in the absence of the EGF receptor ligand, the method further includes a period of no administration of any of the agent or the composition. The diabetic subject for example has recent onset diabetes. Further, following the period of no administration, the composition and the agent are formulated for sequential administration. In certain embodiments, each of the EGF receptor ligand, the gastrin/CCK receptor ligand, and the immunosuppressing agent are formulated in an effective dose. The composition or agent further is some embodiments is formulated with a pharmaceutically acceptable buffer.

Yet another feature of the invention is a method of manufacture of a medicament for use in treating a diabetic subject, the method comprising administering to the subject a composition for islet neogenesis therapy consisting of at least one of EGF51N and gastrin17, and administering at least one immunosuppressing agent. The at least one agent is formulated to be an effective dose of each of Tacrolimus and Sirolimus. Alternatively, the method further involves formulating an effective dose of at least one of EGF51N and gastrin 17, and formulating an effective dose of at least one of Tacrolimus, Everolimus, daclizumab, ISAtx247, and Sirolimus.

Alternatively, the method comprising formulating for use with the subject a gastrin/CCK receptor ligand and an agent for suppressing an immune response. For example, the gastrin/CCK receptor ligand is gastrin17. The agent for suppressing immune response is a drug, for example, the agent for suppressing immune response is selected from at least one of the group consisting of: a rapamycin; a corticosteroid; an azathioprine; mycophenolate mofetil; a cyclosporine; a cyclophosphamide; a methotrexate; a 6-mercaptopurine; an FK506; an ISAtx247; a 15-deoxyspergualin; an FTY 720; a mitoxantrone; a 2-amino-1,3-propanediol; a 2-amino-2[2-(4-octylphenyl)ethyl]propane-1,3-diol hydrochloride; a 6-(3-dimethyl-aminopropionyl) forskolin; and a demethimmunomycin. For example, the rapamycin is Sirolimus or Everolimus. For example, the corticosteroid is dexamethasone.

Alternatively in embodiments of this method, the agent for suppressing immune response is a protein, for example, the protein comprises an amino acid sequence of an antibody. For example, the agent for suppressing immune response is at least one selected from the group consisting of: huI 124; BTI-322; allotrap-HLA-B270; OKT4A; Enlimomab; ABX-CBL; OKT3; ATGAM; basiliximab; daclizumab; antithymocyte immunoglobulin; ISAtx247; Medi-500; Medi-507; Alefacept; efalizumab; and infliximab. The method involves formulating the gastrin/CCK receptor ligand and the agent for suppressing immune response administered sequentially. Further, the gastrin/CCK receptor ligand is administered as a bolus. For example, administering the receptor ligand is further using a route selected from the group consisting of intravenous, subcutaneous, intraperitoneal, and intramuscular. Administering the agent for suppressing immune response is using a route selected from the group consisting of an oral, systemic, intravenous, subcutaneous, intraperitoneal, and intramuscular routes of delivery. In one embodiment of the method, the agent for suppressing immune response is selected from at least one of Tacrolimus, ISAtx247, Everolimus, Sirolimus, and daclizumab.

In any of the embodiments of the methods herein, the invention additionally involves measuring a physiological parameter in the subject, for example, measuring level of: fasting blood glucose; pancreatic insulin content; pancreatic β cell content; and plasma insulin C peptide. The subject is a mammal, for example, the subject is a diabetic mammal, for example, the subject is a diabetic mammal with recent onset diabetes, for example, the subject is a human.

The invention also features a method of treating a diabetic subject, the method comprising administering to the subject a composition comprising an effective dose of gastrin17 and an effective dose of at least one immunosuppressing agent. At least one of the immunosuppressing agents is Tacrolimus or Sirolimus. The method can further involve administering to a subject an effective dose of ISAtx247 or daclizumab. The administered composition further includes a pharmaceutically acceptable buffer.

Also featured is a pharmaceutical composition comprising an agent for suppressing an immune response and at least one of an EGF receptor ligand and a gastrin/CCK receptor ligand the gastrin/CCK receptor ligand is a gastrin. For example, the gastrin/CCK receptor ligand is a gastrin17, and the gastrin17 is gastrin 17Met15 or gastrin17Leu15. Further, the EGF receptor ligand is EGF, for example, the EGF is recombinant human EGF51N. Further, the agent for suppressing immune response is a drug. For example, the agent for suppressing immune response is at least one selected from of the group consisting of a rapamycin; a corticosteroid; an azathioprine; mycophenolate mofetil; a cyclosporine; a cyclophosphamide; a methotrexate; a 6-mercaptopurine; FK506 (Tacrolimus); 15-deoxyspergualin; an FTY 720; a mitoxantrone; a 2-amino-1,3-propanediol; a 2-amino-2[2-(4-octylphenyl) ethyl]propane-1,3-diol hydrochloride; a 6-(3-dimethyl-minopropionyl)forskolin; and a demethimmunomycin. Alternatively, the agent for suppressing immune response is a protein. For example, the agent for suppressing immune response is a portion of an antibody, for example, the agent is at least one selected from the group consisting of: huI 124; BTI-322; allotrap-HLA-B270; OKT4A; Enlimomab; ABX-CBL; OKT3; ATGAM; basiliximab; daclizumab; antithymocyte immunoglobulin; ISAtx247; Medi-500; Medi-507; Alefacept; efalizumab; infliximab; and an interferon.

Another aspect is a kit for treatment of a diabetic subject, comprising a composition for islet neogenesis therapy, an immunosuppressive agent, and a container. The kit includes at least one dose of any one or more of the compositions herein. The kit can further include instructions for use.

Also featured is a method of manufacture of a medicament for use in treating a diabetic subject, the method comprising manufacture of a composition comprising an effective dose of gastrin17 and an effective dose of at least one immunosuppressing agent. For example, a method of manufacture of a medicament for use in treating a diabetic subject, such that the medicament has an effective dose of gastrin17 and an effective dose of each of Tacrolimus and Sirolimus. Also featured is use of an effective dose of each of gastrin17 and at least one immunosuppressing agent in manufacture of a composition for treating a diabetic subject. Also featured is use of an effective dose of gastrin17 and an effective dose of each of Tacrolimus and Sirolimus in manufacture of a medicament for treating a diabetic subject. Also featured is use of an iumunosuppressing agent and at least one of an EGF receptor ligand and a gastrin/CCK receptor ligand for the manufacture of a medicament for treating a diabetic subject.

Alternative diabetes therapies to glucose monitoring and insulin injection have previously been limited by immune rejection of insulin and the β-cells that produce insulin. Administration of an agent for immune suppression with a composition for islet neogenesis therapy (I.N.T.™; U.S. Pat. Nos. 5,885,956 and 6,288,301) would be highly advantageous for treatment of diabetes.

A feature of the present invention is a method of treating a diabetic subject by administering to the subject a composition for islet neogenesis therapy (I.N.T.™), and an agent for suppressing immune response. The agent can be a protein, for example, all or a portion of an antibody. Alternatively, the agent can be a drug, which as used herein means a low molecular weight compound, having a molecular weight of less than about 5,000 daltons, less than about 2,000 daltons, or less than about 1,000 daltons. The composition for islet neogenesis therapy comprises an EGF receptor ligand, for example, the EGF receptor ligand is a recombinant human EGF. For example, the EGF receptor ligand is EGF51N. Further, the composition for islet neogenesis therapy comprises a gastrin/cholecystekinin (CCK) receptor ligand. For example, the gastrin/CCK receptor ligand is human gastrin17 having a leu at position 15.

The agent for suppressing immune response can be at least one of a rapamycin; a corticosteroid; an azathioprine; mycophenolate mofetil; a cyclosporine (cyclosporin); a cyclophosphamide; a methotrexate; a 6-mercaptopurine; a FK506; 15-deoxyspergualin; an FTY 720; a mitoxantrone; a 2-amino-1,3-propanediol; a 2-amino-2[2-(4-octylphenyl) ethyl]propane-1,3-diol hydrochloride; a 6-(3-dimethyl-aminopropionyl) forskolin; or a demethimmunomycin. The term "a rapamycin" means any related chemical entity or derivative that substantially shares the rapamycin pharmacore and shares an immunosuppressive activity. The terms "corticosteroid" means any related chemical entity that substantially shares the immunosuppressive activity. For example, the term rapamycin includes Sirolimus (which is rapamycin) and SDZ-RAD, also known as Everolimus. An example of a corticosteroid is dexamethasone.

Alternatively, the agent for suppressing immune response that is the protein comprises an amino acid sequence of an antibody. For example, the agent is at least one of hul 124; BTI-322; allotrap-HLA-B270; OKT4A; Enlimomab; ABX-CBL; OKT3; ATGAM; basiliximab; daclizumab; antithymocyte immunoglobulin; ISAtx247; Medi-500; Medi-507; Alefacept; efalizumab; infliximab. Yet another alternative is that the agent for suppressing immune response is a protein that is not an antibody, for example, is Glial fibrillary acidic protein (GFAP), or is another glial protein, S100β (Selinfreund, R. et al. J Cell Biol. 1990, 111: 2021-2028), or is an interferon. In yet another embodiment, the agent for suppressing immune response comprises a population of co-polymer molecules having a subset of amino acid residues in random amino sequence. For example, the co-polymer is glatiramer acetate (also known as Copaxone™).

In some embodiments, the islet neogenesis therapy composition and the agent for suppressing immune response are administered simultaneously. Alternatively, the islet neogenesis therapy composition and the agent for suppressing immune response are administered sequentially. Simultaneous administration can be administering the composition and the agent together in a combination, or separately and within about 15 min., about 30 min., or about one hour or even within about one day of each other. Sequential administration means that more than one about day elapses between administering the islet neogenesis therapy composition and the immunosuppressive agent, for example, about one week, about two weeks, or about six weeks elapses between administering the I.N.T.™ composition and the immunosuppressive agent.

In a possible embodiments for treating diabetic patients, the immunosuppressive agent is administered over a course of about several days or about a week, and the I.N.T.™ composition is administered later, for example, after a period of administration of neither the agent nor the composition. The period of administering neither the composition nor the agent can be used to monitor the patient to determine whether a change in immunosuppression in the patient can be observed. In an alternative embodiment, the I.N.T.™ composition is administered over a course of about several days or about a week or about several weeks, and the immunosuppressive agent is administered later, for example, after a period of administration of neither the agent nor the composition. In yet another alternative embodiment, both the I.N.T.™ composition and the immunosuppressive agent can be administered, and the I.N.T.™ composition is then stopped while immunosuppression is continued. In yet another embodiment, the I.N.T.™ composition and the immunosuppressive agent combination is administered, followed by treatment with a combination of a gastrin/CCK ligand and immunosuppressive agent. As used herein, the term "an" can also mean "at least one", so that, for example, an immunosuppressive agent can be two or more immunosuppressive agents administered to effect successful suppression of immune reaction.

The islet neogenesis therapy composition is administered systemically, for example, is administered as a bolus, by a route selected from the group consisting of intravenous, subcutaneous (sc), intraperitoneal (ip), and intramuscular (im). Intravenous administration can be administered as an infusion (drip) or as a bolus. The agent for suppressing immune response can be administered orally, for example if the agent is an orally available drug. Alternatively, the agent for suppressing immune response is administered systemically, for example, by a route selected from the group consisting of intravenous, subcutaneous, intraperitoneal, and intramuscular. The agent for suppressing immune response can be, for example, at least one of Tacrolimus, Sirolimus, and daclizumab.

The method can further comprise measuring a physiological parameter in the subject such as the level of fasting blood glucose; pancreatic insulin content; pancreatic β cell content; and pancreatic islet content. The subject is a diabetic non-human mammal, for example, the subject is a non-obese diabetic (NOD) mouse. In the latter subject, the method can further comprise evaluating the extent of survival in the absence of administration of insulin. Alternatively, the subject is a human, for example, the subject is a human patient, for example, is a human diabetes patient, for example, is a human with a form of diabetes, and is in need of treatment.

Another embodiment provided is a method of treating a diabetic subject, the method comprising administering to the subject a composition for islet neogenesis therapy consisting of an effective dose of at least one of EGF51N and gastrin 17, and administering an effective dose of at least one immunosuppressing agent. Yet another embodiment provided is a method of treating a diabetic subject, the method comprising administering to the subject a composition for islet neogenesis therapy consisting of an effective dose of at least one of EGF51N and gastrin 17, and administering an effective dose of each of Tacrolimus and Sirolimus. Yet another embodiment provided is a method of treating a diabetic subject, the method comprising administering to the subject a composition for islet neogenesis therapy consisting of an effective dose of at least one of EGF51N and gastrin 17, and administering an effective dose of at least one of Tacrolimus, daclizumab, and Sirolimus. The composition or agent can further include a pharmaceutically acceptable buffer.

Also provided herein is a kit for treatment of a diabetic subject, comprising an immunosuppressive agent, an I.N.T.™ composition, and a container. The kit can further comprise instructions for use.

A pharmaceutical composition for treating diabetes comprising a gastrin/cholecystokinin (CCK) receptor ligand and an agent for suppression of immune response is provided. The gastrin/CCK receptor ligand is, in one embodiment, a gastrin, for example, gastrin17Met15, or gastrin17Leu15.

The pharmaceutical composition is formulated, for example, for parenteral administration. Alternatively, the pharmaceutical composition is formulated for oral administration, formulated for parenteral administration, or formulated for a route of administration selected from the group consisting of subcutaneous, intraperitoneal (i.p.), intravenous (i.v.), and intramuscular injection. The composition is formulated for systemic administration. The composition is formulated for a route of administration selected from the group consisting of transdermal and mucosal delivery.

A feature of the present invention is a method of treating a diabetic subject by administering to the subject a composition comprising a gastrin/CCK ligand receptor, and an agent for suppressing immune response. The agent can be a protein, for example, all or a portion of an antibody. Alternatively, the agent can be a drug, which as used herein means a low molecular mass compound, having a molecular weight of for example, less than about 5,000 daltons, less than about 2,000 daltons, or less than about 1,000 daltons.

Further, the gastrin/CCK receptor comprises gastrin 17, for example, the gastrin/CCK receptor ligand is human gastrin17 having a leu at position 15, or having a met at position 15.

The agent for suppressing immune response can be at least one of a rapamycin; a corticosteroid; an azathioprine; mycophenolate mofetil; a cyclosporine; a cyclophosphamide; a methotrexate; a 6-mercaptopurine; a FK506; ISAtx247; 15-deoxyspergualin; an FTY 720; a mitoxantrone; a 2-amino-1,3-propanediol; a 2-amino-2[2-(4-octylphenyl) ethyl]propane-1,3-diol hydrochloride; a 6-(3-dimethyl-aminopropionyl) forskolin; or a demethimmunomycin. For example, the rapamycin is SDZ-RAD. For example, the corticosteroid is dexamethasone. Other agents capable of suppressing immune response are considered within the scope of the composition with use of a gastrin/CCK receptor ligand. Alternatively, the agent is the protein that comprises an amino acid sequence of an antibody. For example, the agent is at least one of: huI 124; BTI-322; allotrap-HLA-B270; OKT4A; Enlimomab; ABX-CBL; OKT3; ATGAM; basiliximab; daclizumab; antithymocyte immunoglobulin; ISAtx247; Medi-500; Medi-507; Alefacept; efalizumab; or infliximab. In a different embodiment, the agent for suppressing immune response can be a naturally occurring cytokine or chemokine, such as an interferon or a glial protein such as GFAP or S100β. In yet another embodiment, the agent for suppressing immune response comprises a population of co-polymer molecules having a subset of amino acid residues in random amino sequence. For example, the co-polymer is glatiramer acetate, or another copolymer comprising amino acids (see, for example, Fridkis-Hareli et al., 2002, J. Clin. Inves. 109: 1635-1643).

In some embodiments, the gastrin/CCK receptor ligand and the agent for suppressing immune response are administered simultaneously. Alternatively, the gastrin/CCK receptor ligand and the agent for suppressing immune response are administered sequentially. Simultaneous administration can be administering the gastrin/CCK receptor ligand and the agent together in a combination, or separately and within minutes, for example, 15 min., 30 min., or within hours, for example, one hour, four hours, or even within one day of each other. Sequential administration means that more than one day elapses between administering the gastrin/CCK receptor ligand and the agent for suppressing immune response. In an embodiment of a method for treating diabetic patients, the immunosuppressive agent is administered over a course of several days or about a week, and the gastrin/CCK receptor ligand is administered later, for example, after a period of administration of neither the agent nor the receptor ligand.

The period of administering neither the agent nor the receptor ligand is used to monitor the patient to determine whether a change in immunosuppression in the patient can be observed. In an alternative embodiment, both the gastrin/CCK receptor ligand and the agent that suppresses immune response can be first administered in combination, and then administration of the gastrin/CCK receptor ligand is discontinued and administration of the agent that suppresses immune response is continued. An alternative embodiment herein is a method of treating a diabetic patient comprising administering an I.N.T.™ composition for a period of time. The period of time may be at least one day, for example, several days, for example, at least one week, for example several weeks, for example, at least six weeks, followed by administration of at least one immunosuppressive agent.

The gastrin/CCK receptor ligand is administered systemically, for example, is administered as a bolus, by a route selected from the group consisting of intravenous, subcutaneous, intraperitoneal, and intramuscular. Intravenous administration can be administered as an infusion (drip) or as a bolus. The agent for suppressing immune response can be administered orally, for example if the agent is an orally available drug. Alternatively, the agent for suppressing immune response is administered systemically, for example, by a route selected from the group consisting of intravenous, subcutaneous, intraperitoneal, and intramuscular. The agent for suppressing immune response can be, for example, at least one of Tacrolimus, Sirolimus, ISAtx247, and daclizumab.

The method can further comprise measuring a physiological parameter in the subject such as the level of fasting blood glucose; pancreatic insulin content; pancreatic β cell content; and pancreatic islet content. The subject is a diabetic non-human mammal, for example, the subject is a non-obese diabetic (NOD) mouse. In the latter subject, the method can further comprise evaluating the extent of survival in the absence of administration of insulin. Alternatively, the subject is a human patient, for example, with an indication of a form of diabetes, and in need of treatment.

Another embodiment provided herein is a method of treating a diabetic subject, the method comprising administering to the subject a gastrin/CCK receptor ligand consisting of an effective dose of gastrin17, and administering an effective dose of at least one immunosuppressing agent. Yet another embodiment provided is a method of treating a diabetic subject, the method comprising administering to the subject a composition gastrin/CCK receptor ligand comprising an effective dose of at least one of gastrin17, and administering an effective dose of each of Tacrolimus and Sirolimus. Yet another embodiment provided is a method of treating a diabetic subject, the method comprising administering to the subject a gastrin/CCK receptor ligand consisting of an effective dose of gastrin17, and administering an effective dose of at least one of Tacrolimus, daclizumab, ISAtx247, and Sirolimus. The compositions or agents herein can further include a pharmaceutically acceptable buffer.

Also provided herein is a kit for treatment of a diabetic subject, comprising an immunosuppressive agent, a gastrin/CCK receptor ligand, and a container. The kit can further comprise instructions for use. Any of the bits herein can further comprise a unit dose, i.e., an effective dose, of either or both of the composition and at least one agent therein.

DETAILED DESCRIPTION OF THE INVENTION

Figure 1:
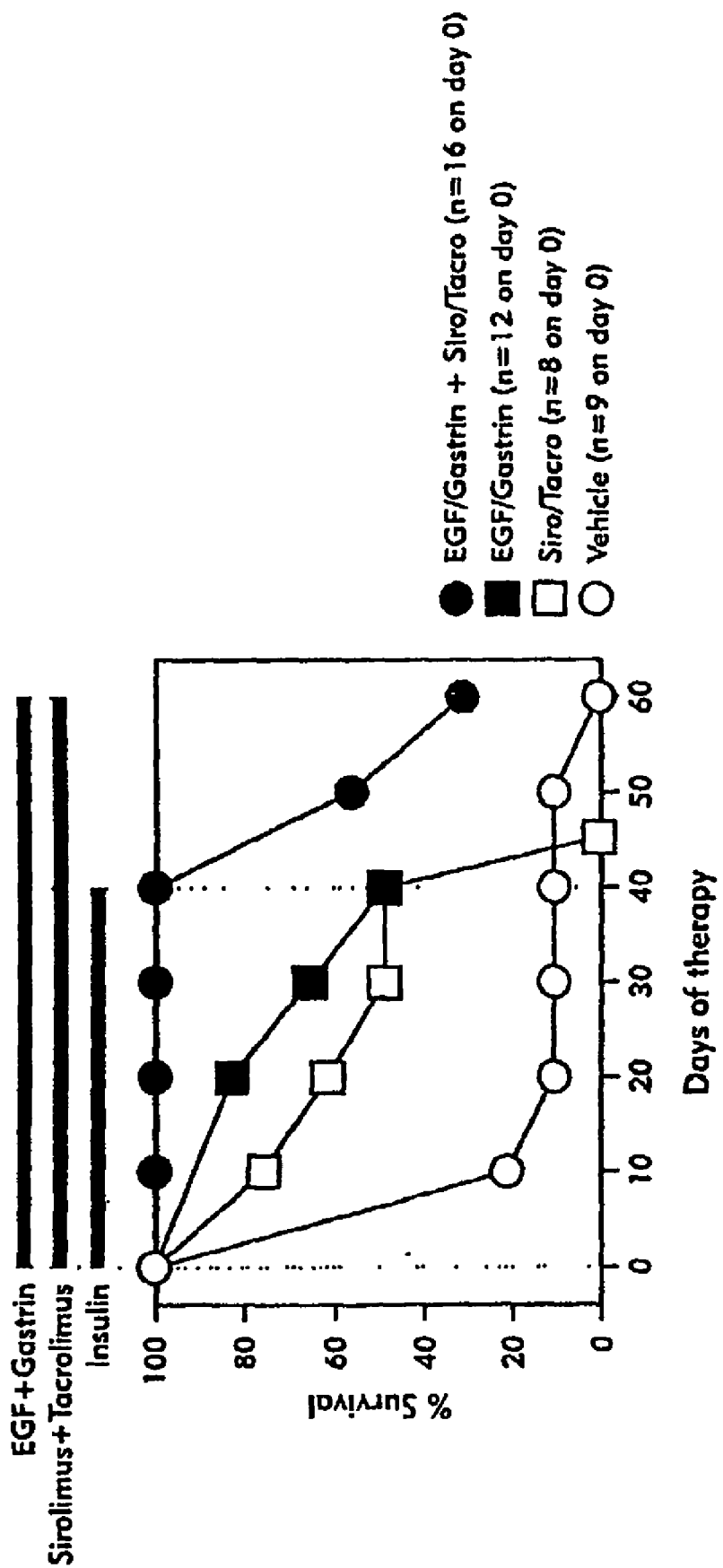
FIG. 1 is a line graph showing percent survival on the ordinate of NOD mice in each of four groups as described in Example 1, as a function of time in days on the abscissa. Starting at week 4, Group 1 animals (solid circles) were administered concurrently an I.N.T.™ composition (Gastrin and EGF) and immunosuppression drugs (Sirolimus and Tacrolimus); Group 2 animals (solid squares) were administered the I.N.T.™ composition only; Group 3 animals (open squares) were administered the immunosuppression drugs only; and Group 4 animals (open circles) were administered vehicle only.

The invention in one aspect features islet neogenesis therapy (I.N.T.™) compositions and methods, for example, gastrin and EGF in combination with immunosuppressive agents, to stimulate the growth of new β cells in vivo, increasing islet mass, and result in improved glucose tolerance in diabetic subjects, for example, in diabetic humans and in animals.

The gastrin/CCK receptor ligand and the EGF receptor ligand can be administered in a single combined dose, or administered separately in any order. An "effective combined dose" of these compositions is one which produces an increase in number of insulin secreting cells, or an increase in insulin blood level, or an increase in β-cell mass. The gastrin/CCK receptor ligand is, in one embodiment, human gastrin of length 17 amino acid residues, the residue at position 15 being leucine (1-17Leu15, referred to herein as gastrin17leu15); further, the EGF receptor ligand is human EGF51N. The effective dose can contain a ratio of gastrin/CCK receptor ligand to EGF receptor ligand that is greater than 1, for example, the effective dose contains a ratio of gastrin/CCK receptor ligand to EGF receptor ligand greater than 10. A convenient route of administering the dose is with a systemic injection, for example, a subcutaneous bolus.

In a further embodiment, the recipient subject is administered an agent that suppresses the immune system. For example, the agent is a low molecular weight organic chemical, for example, is at least one of Tacrolimus, Sirolimus, cyclosporine, and cortisone and other drugs as shown in Table 1. In an alternative embodiment, the agent is an antibody, for example, the antibody is anti-CD11a and other antibodies also shown in Table 1. In yet another alternative, the immunosuppressive agent can be an antibody that is elaborated by the subject following an immunization schedule, for example, against GFAP or against S100β. The subject can be diabetic, for example, the subject is a non-obese diabetic mouse (the NOD mouse) or a streptozoticin-treated mouse. The subject can be a human, for example a diabetic patient having type I or type II diabetes, or having gestational diabetes, or having had diabetes in the past, for example, having had gestational diabetes in a past pregnancy.

Further, evaluating the size and function of newly developed β insulin secreting cells or islets is measuring a parameter selected from the group of: islet β cell mass, islet β cell number, islet β cell percent, blood glucose, serum glucose, blood glycosylated hemoglobin, pancreatic β cell mass, pancreatic β cell number, fasting plasma C peptide content, serum insulin, and pancreatic insulin content.

As diabetes is in certain cases an autoimmune disease, an embodiment of I.N.T.™ is systemic administration of therapeutically effective doses of, for example, the ligands of receptors for each of EGF and gastrin/CCK, such as a combination of a gastrin and an EGF, to subjects or patients who are also treated with one or more agents that suppress the immune system, i.e., immunosuppressive agents. The gastrin and EGF combination would be administered systemically as described for the treatment of diabetic patients where the goal is to stimulate neogenesis of islets formed de novo within the pancreas (see U.S. Pat. Nos. 5,885,956 and 6,288,301).

A number of different endpoints can be used to determine whether gastrin and EGF treatment, or treatment with the combination of gastrin and EGF and an immunosuppressive agent, increases the functional mass of β cells in the islet transplants. These include measurement of enhanced plasma levels of circulating human C peptide and human insulin, after injecting mice with β cell stimulants such as glucose or arginine; a response to gastrin/EGF treatment demonstrated by increased human insulin immunoreactivity or mRNA levels extracted from the islet transplants; and increased number of β cells, determined by morphometric measurement of islets in treated animals. Enhanced β cell function of human islets can also be demonstrated by reversal of the hyperglycemia in recipient mice with streptozotocin induced or genetic (NOD) diabetes. In Examples herein, enhanced β cell function after treatment of the diabetic recipient subject with gastrin, with EGF and with one or more immunosuppressive agents was demonstrated by improved survival upon withdrawal of insulin, and by correcting hyperglycemia as indicated by fasting blood glucose level. Further, increases in both pancreatic insulin and plasma C-peptide were observed.

TABLE 1

Exemplary agents for immune suppression, and commercial sources

| Names | Company | Nature |
| --- | --- | --- |
| 2-amino-1,3-propanediol derivatives | Novartis | Used for preventing or treating chronic rejection in a patient receiving an organ or tissue allo-or xeno-transplant |
| 2-amino-2[2-(4-octylphenyl)ethyl]propane-1,3-diol hydrochloride | Yoshitomi Pharmaceutical Industries, Ltd | Immunosuppression, from accelerated lymphocyte homing |
| 40-O-(2-hydroxyethyl)-rapamycin, SDZ-RAD, Everolimus (Certican ®) | Novartis Pharmaceuticals | Sirolimus (rapamycin) derivative, used for acute kidney rejection; reduces rejection and graft vasculopathy following |

TABLE 1-continued

Exemplary agents for immune suppression, and commercial sources

| Names | Company | Nature |
|---|---|---|
| 6-(3-dimethyl-aminopropionyl) forskolin | Matsumori Akia Nippon Kayaju Co Ltd | heart transplantation by inhibiting cell proliferation Immunosuppressing action useful also for treating autoimmune disease |
| 6-mercaptopurine (Purinethol ®, 6-MP) | Glaxo SmithKline | Used to treat Crohn's disease, inflammatory bowel disease and for organ transplant therapy |
| ABX-CBL (CBL-1) | Abgenix | Mouse monoclonal AB targeted against human T-cell, B cells, NK cells and monocytes, for treatment of steroid-resistant graft vs host diseases, potential use in treatment of inflammatory and autoimmune disorders |
| Alefacept (human LFA-3 IgG1 fusion protein, AMEVIVE ®) | University of Utah-Dermatology Dept/BIOGEN | Knocks out causative memory T-lymphocytes; Used to treat psoriasis, a T-cell mediated inflammatory disorder |
| HLA-B2702 peptide (Allotrap ®) | SangStat Medical | Human peptide, blocks action of NK cells and T-cell mediated toxicities, used for prevention of first kidney allograft rejection |
| Antisense ICAM-1 inhibitor (ISIS 2302), Enlimomab, BIRR1, Alicaforsen) | ISIS-Boehringer Ingleheim | Mouse monoclonal AB blocks white blood cell adhesion to T-cell surface molecule (ICAM-1r); treatment of kidney transplant rejection |
| Azathioprine (Imuran ®, Azasan ®) | Generic, Glaxo SmithKline, Prometheus Laboratories, aaiPharma | Treatment of rheumatoid arthritis and prevention of kidney transplant rejection, and other autoimmune or inflammatory disorders such as inflammatory bowel disease |
| BTI-322 | MedImmune | Mouse derived monoclonal AB targeted to CD2 receptor; used for prevention of first-time kidney rejection, and treatment of resistant rejection |
| Cladribine (Leustatin ®) | Boehringer Ingleheim | Antimetabolite and immunosuppressive agent that is relatively selective for lymphocytes; used to treat lymphoid malignancies, e.g., hairy-cell leukemia. |
| Cyclophosphamide (CTX, Neosar ®, Cytoxan ®, Procytox ®) | Generic | Immunosuppressant t for treatment of arthritis and other auto-immune disorders and cancers |
| Cyclosporine (cyclosporin A, cyclosporin) (Sandimmune ®, Neoral ®, SangCya ®) | Novartis | 11 amino acid cyclic peptide; blocks helper T-cell, immunosuppressant used in organ transplant therapy and other immune diseases |
| Demethimmunomycin" (L-683,742: also described as 31-desmethoxy-31-hydroxy-L-683,590) | Merck & Co | Treatment of autoimmune diseases, infectious diseases and/or prevention of organ transplant rejections |
| Dexamethasone (Decadron, Dexone, Dexasone) | Generic | An adrenocorticoid, effective immunosuppressant in various disorders |
| Docosahexaenoic acid (DHA) | Not applicable | Immunosuppressant by that lowers the proportion of T |

TABLE 1-continued

Exemplary agents for immune suppression, and commercial sources

| Names | Company | Nature |
|---|---|---|
| | | cells expressing CD4 or CD8, blocks antigen recognition process; Taku et al., Journal of Agricultural and Food Chemistry, 2000; 48(4):1047 |
| FTY720 (oral myriocin derivative) | Novartis Pharmaceuticals | Alters lymphocyte infiltration into grafted tissues; used for prevention of organ rejection in kidney transplants |
| Glatiramer acetate (copolymer-1, Copaxone ®) | Teva Pharmaceuticals | Synthetic peptide copolymer; decoy that mimics structure of myelin so immune cells bind Copaxone instead of myelin; for multiple sclerosis |
| Glial fibrillary acidic protein (GFAP) | CalBiochem; Synx Pharma | Possesses immunosuppressive activities in diabetic animal models; Winer et al., Nature Medicine 9:198 (2003) |
| Gusperimus, (15-deoxyspergualin (Spanidin ®) | Bristol Myers-Squibb | Intravenous immunosuppressant; suppresses production of cytotoxic T-cells, neutrophils and macrophages |
| hu1124 (anti-CD11a) | XOMA | Humanized monoclonal antibody; targets CD11a receptor on surface of T cells to selectively inhibit immune system rejection of transplanted organs |
| Infliximab (Remicade ®) | Centocor (affiliate of Johnson and Johnson) | Monoclonal AB, binds and inactivates human TNF-alpha and; used to treat Crohn's disease and rheumatoid arthritis |
| Interferon | Various companies including Serono, Biogen etc | Immunomodulatory properties |
| ISAtx247 | Isotechnika | Used to treat autoimmune diseases such as rheumatoid arthritis and psoriasis |
| isotretinoin | | Immunosuppressant, reduces ability of T cells to proliferate in response to immune challenge. Vergelli et al., Immunopharmacology, 1997, 31:191. |
| Medi-500 (T10B9) | MedImmune | Intravenous monoclonal AB that targets human T-cells; treats acute kidney rejection and graft-vs-host disease |
| Medi-507 | MedImmune/Bio-Transplant | Intravenous humanized AB directed against CD2 T-cell; used to treat corticosteroid-resistant graft vs host disease and prevention of kidney rejection |
| Methotrexate (Rheumatrex ®, Amethopterin, Trexall ®) | Wyeth Lederle, Generic | Antimetabolite used to treat Crohn's disease, severe psoriasis, and adult rheumatoid arthritis (and as an anti-cancer drug) |
| Mitoxantrone (Novantrone ®) | Immunex | Antiproliferative effect on cellular immune system including T-cells, B-cells and macrophages; used to treat hormone-refractory prostate cancer, acute |

TABLE 1-continued

Exemplary agents for immune suppression, and commercial sources

| Names | Company | Nature |
|---|---|---|
| mycophenolate mofetil (CellCept ®) | Roche | myelogenous leukemia and multiple sclerosis Proliferation of T and B lymphocytes by blocking the synthesis of purine nucleotides; used in organ transplant therapy and inflammatory bowel disease |
| OKT4A | R. W. Johnson Pharmaceutical Research Institute | Mouse monoclonal AB targeted against human CD4 T cell; used for prevention of kidney transplant rejection when used in combination with other immunosuppressant drugs |
| Muromonab-CD3 (Orthoclone OKT3 ®)( ) | R. W. Johnson Pharmaceutical Research Institute | Monoclonal AB that binds to receptor sites on T-cells, preventing activation by transplanted tissue |
| Prednisolone (Deltasone ®, Oraone ®) | | Corticosteroid, suppresses inflammation associated with transplant rejection |
| basiliximab (Simulect ®) | Novartis Pharmaceuticals | Monoclonal AB that binds to receptor sites on T-cells, preventing activation by transplanted tissue (renal transplant) |
| S100β | glial protein | Possesses immunosuppressive activities in diabetic animal models |
| Sirolimus, Rapamycin (Rapamune ®) | Wyeth-Ayerst Laboratories | Immunosuppressant and potent inhibitor of cytokine (e.g.IL-2)-dependent T-cell proliferation (kidney transplant) |
| Tacrolimus (Prograf; FK-506) | Fujisawa | Interferes with IL-2 TCR communication |
| Antithymocyte immunoglobulin (ATGAM, Thymoglobulin ®) | SangStat Medical Corporation, Pharmacia and Upjohn | Anti-human thymocyte immunoglobulin; used in reversal of acute kidney transplant rejection and will likely be used off-label for transplant induction therapy |
| efalizumab (Xanelim ®) | XOMA | T-cell modulator that target T-cells through interactions with adhesion molecules on endothelial cell surface, target migration of T-cells into the skin and target activation of T-cells; Used to treat Psoriasis |
| Daclizumab (Zenapax ®), HAT (Humanized Anti-Tac), SMART anti-Tac, anti-CD25, and humanized anti-IL2-receptor | Protein Design Laboratories/Roche | Monoclonal AB inhibits binding of IL-2 to IL-2 receptor by binding to IL-2 receptor; suppresses T cell activity against allografts (renal transplant) |

The methods and compositions herein increase the confidence that clinical trials of treatment with gastrin and EGF and an immunosuppressive agent will show stimulation of endogenous β islet cell growth within the pancreas in type I and type II diabetic patients.

As used herein, the term "gastrin/CCK receptor ligand" encompasses compounds that stimulate the gastrin/CCK receptor such that when EGF receptors in the same or adjacent tissue or in the same individual are also stimulated, neogenesis of insulin-producing pancreatic islet cells is induced. Examples of such gastrin/CCK receptor ligands are given in U.S. Pat. No. 6,288,301, and include various forms of gastrin, such as gastrin 34 (big gastrin), gastrin 17 (little gastrin), and gastrin 8 (mini gastrin); various forms of cholecystokinin such as CCK 58, CCK 33, CCK 22, CCK 12 and CCK 8; and other gastrin/CCK receptor ligands that demonstrate the same synergistic activity with EGF receptor ligands, and which can induce differentiation of cells of mature pancreas to form insulin-secreting islet cells, when acting synergistically with an EGF receptor ligand. Also contemplated are active analogs, fragments and other modifications of the above, including both peptide and non-peptide agonists or partial agonists of the gastrin/CCK receptor such as A71378 (Lin et al, Am. J. Physiol. 258 (4 Pt 1): G648, 1990) that either alone or in combination with EGF receptor ligands induce differentiation of cells in mature pancreas to form insulin-secreting islet cells.

Small forms of gastrin such as gastrin 17 are economically prepared by peptide synthesis, and the synthetic peptides are commercially available. Synthetic human gastrin 17, and derivatives such as human gastrin 17 having leucine in place of methionine at position 15 as used in Examples herein, are also available from Bachem AG, Bubendorf, Switzerland, and from Researchplus, Nanasquan, N.Y.

Gastrin/CCK receptor ligands include also active analogs, fragments and other modifications of the above ligands. Such ligands also include compounds that increase the secretion of endogenous gastrins, cholecystokinins or similarly active peptides from sites of tissue storage. Examples of these are the gastric releasing peptide, omeprazole which inhibits gastric acid secretion, and soya bean trypsin inhibitor which increases CCK stimulation.

As used herein, the term "EGF receptor ligand" encompasses compounds that stimulate the EGF receptor such that when gastrin/CCK receptors in the same or adjacent tissue or in the same individual are also stimulated, neogenesis of insulin-producing pancreatic islet cells is induced. Examples of such EGF receptor ligands include full length EGF which is EGF1-53, and further include EGF148, EGF1-49, EGF1-52, and fragments and active analogs thereof. Other examples of EGF receptor ligands are TGFα forms that include 1-48, 1-47, 1-51, and amphiregulin and pox virus growth factor as well as any EGF receptor ligands that demonstrate the same synergistic activity with gastrin/CCK receptor ligands. These include active analogs, fragments and modifications of the above. See also, Carpenter and Wahl, Chapter 4, in *Peptide Growth Factors* (Eds. Sporn and Roberts), Springer Verlag, 1990.

The group of compounds which are EGF receptor ligands further includes "modified EGF", which are variants of normal or wild-type EGF. Modifications have been shown to affect one or more biological activity such as the rate of clearance of EGF. The term includes peptides having an amino acid sequence substantially similar to that of human EGF, for example, with one or a few amino acid substitutions at various residue positions.

Recombinant EGF forms have been genetically engineered to have alterations in structure and activities, for example, EGF having a methionine at position 21 replaced by a leucine residue has been described (U.S. Pat. No. 4,760,023). Recombinant human EGF (HEGF) having 51 residues, i.e., lacking the two C-terminal residues at positions 52 and 53 of HEGF, and having a neutral amino acid substitution at position 51, retain EGF activity and are more resistant to protease degradation during a microbial production process, and following administration to a subject. A series of nucleic acid molecules have been described that encode a family of proteins that have significant similarity to EGF and TGFα (WO 00/29438). EGF muteins (mutated EGF) having histidine at residue 16 replaced with a neutral or acidic amino acid have been described (WO 93/03757), such forms retaining activity at low values of pH. Chemical analogues and fragments of EGF and TGFα retain ability to bind various members of the EGF receptor family (U.S. Pat. No. 4,686,283). Various modifications of EGF or TGFα confer advantageous properties affecting one or more of recombinant protein production, in vitro and in vivo stability, and in vivo activity. A preferred recombinant modified EGF receptor ligand used in the Examples herein is a C-terminus deleted form of human EGF of 51 amino acids in length, having asparagine at position 51 (referred to herein as EGF51N), which EGF protein retains substantially full I.N.T.™ activity, and has in vivo and/or in vitro stability that is that is at least about as great or greater than normal or wild type HEGF (U.S. patent application Ser. No. 10/000,840, S. Magil et al., published May 12, 2003 as PCT/US02/33907, and incorporated by reference herein in its entirety).

As used herein, the term "immunosuppressant" means any agent that suppresses immune response. Exemplary immunosuppressant agents are shown in Table 1, and any derivatives of those agents or functional equivalents are considered appropriate for embodiments of the invention as described herein and in the claims.

As used herein, a dosing schedule refers to a protocol for administering an I.N.T.™ composition and one or more of an immunosuppressive agent, each in an effective dose, administered together or separately, and includes the amount of the composition delivered per day, and the duration or period of time over which each composition is administered.

Most insulin dependent diabetic patients require insulin injection at least on a daily basis. Multiple doses per day of insulin are required under certain circumstances of illness or diet for management of diabetes, and the insulin administration is indicated by results of frequent glucose monitoring, another activity which is required of a diabetes patient for optimal management of the disease, which is performed for example as often as five times daily.

Remission from diabetes due to successful islet neogenesis therapy in combination with an immunosuppressive agent is indicated by a decreased fasting blood level of glucose, and by a decreased level and duration of elevated blood glucose in response to a dietary challenge of sugar consumption. Upon achieving successful islet neogenesis, insulin administration is reduced from, for example, five injections to two injections per day; from two injections to one injection per day; and from one to none, as indicated by data obtained from monitoring blood glucose levels. One of ordinary skill in the art of diabetology, when treating a diabetic patient, is familiar with adjusting insulin dosage to levels of blood glucose following fasting and under other physiological conditions.

Dosages of the I.N.T.™ compositions to be administered to a subject are adjusted for known variations from species to species in standard data encompassing criteria for absorption, distribution, half-life kinetics in circulation, metabolism, excretion, and toxicology of the receptor ligands of the embodiments herein, for example, for each primate and rodent species. In general, dosages are adjusted to be about 6-fold to about 100-fold greater for administration to a rodent species than to a primate species.

Immunosuppressive agents in Table 1 or other equivalent agents are administered as supplied by the manufacturers, normalizing to body weight of the subject as is known by one of skill in the pharmacological arts. For example, Tacrolimus is generally administered by injection or orally, Sirolimus is generally administered orally.

Modes of administration of the receptor ligand compositions and immunosuppressive agents include but are not limited to subcutaneous, transdermal, intramuscular, intraperitoneal, intravenous, intranasal, and oral routes. The compounds may be administered by any convenient route, for example by infusion or bolus injection, by pump, by absorption through epithelial or mucocutaneous linings (e.g., oral mucosa, rectal and intestinal mucosa, etc.). The receptor ligands herein may be administered in combination with one or a plurality of other biologically active agents. For example, a recipient of the compositions and methods herein may be administered one or more antibiotics if a bacterial infection is present, or aspirin if a headache is present. Administration of the receptor ligands herein is preferably by a systemic route.

The present invention also provides pharmaceutical compositions. Such compositions comprise a therapeutically effective amount of a therapeutic, and a pharmaceutically acceptable sterile carrier or excipient. Such a carrier includes but is not limit to saline, buffered saline, dextrose, water, glycerol, ethanol, and combinations thereof. The formulation should suit the mode of administration.

The composition, if desired, can also contain minor amounts of wetting or emulsifying agents, such as Tween, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In one embodiment, the composition is formulated in accordance with routine procedures as a pharmaceutical composition adapted for intravenous administration to human beings. Compositions for systemic administration are typically solutions in sterile isotonic aqueous buffer. Where necessary, the composition may also include additional components, for example, a solubilizing agent. Generally, the ingredients are supplied either separately or pre-mixed in unit dosage form. In addition to solution form, the composition can be supplied as a dry lyophilized powder, or as a non-aqueous concentrate, for example, in a hermetically sealed container such as an ampoule or sachette indicating the quantity of active agent. Where the composition is to be administered by infusion, it can be dispensed using an infusion bottle containing sterile pharmaceutical grade water or saline. Where the composition is administered by injection, an ampoule of sterile water or saline for injection can be provided so that the ingredients may be mixed prior to administration.

The therapeutic agent embodiments of compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of each of the therapeutic agents of the compositions herein, and their relative amount with respect to each other which will be effective in the treatment of a particular disorder or condition will depend on the nature of the disorder or condition, and can be determined by standard clinical techniques. The precise dose to be employed in a formulation depends also on route of administration, and the extent of the disease or disorder in a given patient, and should be decided according to the judgment of the practitioner and each patient's circumstances. However, suitable dosage ranges for parenteral administration are generally about 0.01 microgram or one microgram, to about 100, about 200, or to about 500 micrograms of the active compound per kilogram body weight for an EGF receptor ligand. Preferably, the dose range of the EGF receptor ligand is 0.01 micrograms to 100 micrograms per kg body weight. Further, suitable dosage ranges for parenteral administration are generally about 0.1 micrograms or about 0.2 or about 0.5 micrograms to about 2 milligrams, or about 3 milligrams, or to about 5 milligrams per kg body weight for a gastrin receptor ligand. Preferably, the dose range of the gastrin receptor ligand is about 0.1 microgram to 2 milligram per kg body weight.

Effective doses may be extrapolated from dose-response curves derived from in vitro or animal model test systems. A daily dose is administered as a single dose or divided into a plurality of smaller fractional doses, to be administered several times during the day.

Suppositories generally contain active ingredient in the range of about 0.5% to about 10% by weight; oral formulations preferably contain about 10% to about 95% active ingredient by weight.

Embodiments of the invention herein also provide a pharmaceutical pack or kit comprising one or more containers filled with one or more of the ingredients of the pharmaceutical compositions of the invention, for example, a container having a unit dosage of each or both of a gastrin/CCK receptor ligand and an EGF receptor ligand, and one or more of an immunosuppressive agent. Associated with such container(s) can be a notice in the form prescribed by a governmental agency regulating the manufacture, use or sale of pharmaceuticals or biological products, which notice reflects approval by the agency of manufacture, use or sale for human administration. The pack or kit can in certain embodiments include one or more containers, for example, containers having insulin, to be administered, for example, during the dosing schedule prior to induction of islet neogenesis and remission from diabetes.

Without being limited by any particular model or mechanism, it is anticipated that an early onset of diabetes is characterized by a different stage of islet destruction, for example, having a different population of pancreatic cells than is late stage diabetes. For example, it is likely that the early onset diabetes or prediabetic patient has a functional β cell mass and a ligher level of islet cell precursor cells, populations which are likely to be lower, or deficient or lacking in a late stage type I diabetic. For that reason, the invention in another general embodiment provides a method for preventing onset of diabetes or treating diabetes, for example early onset diabetes, the method comprising administering to a mammal in need thereof a composition comprising of a gastrin/CCK receptor ligand and an agent that suppresses an immune response. Further, it is anticipated that such a treatment can be used over a long time period, for prolonged maintenance of the diabetic patient.

The invention in one aspect features a method for expanding a pre-existing functional β cell mass within the subject's islets, or of expanding a functional β cell mass within pancreatic islet transplants in a diabetic mammal recipient of a transplant of purified islets. The method comprises administering a composition comprising an effective dose of each of a gastrin/CCK receptor ligand and agent that suppresses an immune response.

Gastrin in combination with injury can stimulate the growth (proliferation) of new β cells, resulting in increased islet mass (Rooman, I., et al., 2002, Diabetes 51(3), 686-690). Gastrin can effect differentiation of a pancreatic islet precursor cell to a mature insulin-producing cell, thus enhancing islet neogenesis and reversing diabetes symptoms or inhibiting progression of the diabetes.

The gastrin/CCK receptor ligand and immunosuppressive agent can be administered in a single combined dose, or administered separately in any order. An "effective combined dose" of these compositions is one which produces an increase in number of insulin secreting cells, or an increase in insulin blood level, or an increase in β-cell mass. The gastrin/CCK receptor ligand is in one embodiment, human gastrin of length 17 amino acid residues, the residue at position 15 being leucine (gastrin17Leu15); or methionine (gastrin17Met15). A convenient route of administering the dose is with a systemic injection, for example, a subcutaneous bolus.

The subject is administered the gastrin/CCK receptor ligand and an agent that suppresses the immune system. In one embodiment, the agent is a low molecular weight organic chemical, for example, is at least one of Tacrolimus, Sirolimus, ISAtx247, cyclosporin, and cortisone and other drugs as shown in Table 1. In an alternative embodiment, the agent is an antibody, for example, the antibody is anti-CD11a and other antibodies also shown in Table 1. The subject can be a diabetic mammal, for example, a non-obese diabetic mouse, the NOD mouse. The subject can be a human diabetic patient, for example having type I or type II diabetes, or having gestational diabetes, or having had gestational diabetes in the past. Further, evaluating the size and function of newly developed β insulin secreting cells or islets is measuring a parameter selected from the group of: islet β cell mass, islet β cell number, islet β cell percent, blood glucose, serum glucose, blood glycosylated hemoglobin, pancreatic β cell mass, pancreatic β cell number, fasting plasma C peptide content, serum insulin, and pancreatic insulin content.

As diabetes is in certain cases an autoimmune disease, an embodiment is systemic administration of therapeutically effective doses of, for example, a ligand of a receptor for a gastrin/CCK, to subjects or patients who are also treated with one or more agents that suppress immune response (see Table 1).

A number of different endpoints can be used to determine whether treatment with gastrin and the agent that suppresses an immune response increases the functional mass of β cells in the islet transplants. These include measurement of enhanced plasma levels of circulating human C peptide and human insulin, after injecting mice with β cell stimulants such as glucose or arginine; a response to treatment with gastrin and the immunosuppressive agent demonstrated by increased human insulin immunoreactivity or mRNA levels extracted from the islet transplants; and increased number of β cells, determined by morphometric measurement of islets in treated animals. Enhanced β cell function of human islets can also be demonstrated by reversal of the hyperglycemia in recipient mice with streptozotocin induced or genetic (NOD) diabetes.

The methods and compositions herein increase the confidence that clinical trials of treatment with gastrin and an immunosuppressive agent will show stimulation of endogenous β islet cell growth within the pancreas in type I and type II diabetic patients.

The methods herein are also valuable in determining the plasma levels of various compositions, such as the administered gastrin/CCK receptor ligand that stimulates new growth of human islets in vivo, or another endogenous factor that is induced by administered gastrin/CCK receptor ligand. In combination with Phase I pharmacokinetic data, data obtained using these methods can improve the design of clinical studies, by reducing dose exploration studies in human subjects, to determine the effective human dose range.

The agent that suppresses the immune system or the gastrin/CCK receptor ligand is provided in an amount that is sufficient in combination to induce differentiation of the pancreatic islet precursor cells into insulin secreting islet cells for a prolonged period of time.

In general, for treatment with gastrin/CCK receptor ligand and an immunosuppressive agent, as for any of the embodiments herein, the subject can be a mammal such as a human. In addition, the mammal can be a rodent such as a mouse or rat, or a dog, cat, sheep, goat, cow, horse, or an ape such as a gorilla or a chimpanzee.

In another aspect, the invention provides a method for inducing pancreatic islet neogenesis in a mammal, the method comprising administering to the mammal a composition comprising a gastrin/CCK receptor ligand and an agent that suppresses the immune system, each in an amount sufficient to increase cell differentiation of islet precursor cells and inhibit islet destruction in the in pancreas, thereby having a net increase in pancreatic islet neogenesis.

The composition is in a dosage effective for inducing differentiation of an islet precursor cell into a mature insulin secreting cell. The composition can be in a pharmaceutically acceptable carrier, pharmaceutically acceptable buffer, or in a pharmaceutically acceptable salt.

In another aspect, the invention provides a kit for treating or preventing diabetes, containing a composition comprising a gastrin/CCK receptor ligand and an agent that suppresses the immune system, a container, and instructions for use. The composition of the kit can further comprise a pharmaceutically acceptable carrier. The composition of the kit can be present in at least one unit dosage. The kit can comprise insulin in at least one unit dosage.

As used herein, a dosing schedule refers to a protocol for administering a gastrin/CCK receptor ligand and at least one immunosuppressive agent, each in an effective dose, administered together or separately, and includes the amount of the composition delivered per day, and the duration or period of time over which each composition is administered.

Unless otherwise defined, all technical and scientific terms herein have the same meaning as commonly understood by one of ordinary skill in the art to which this invention pertains. Although methods and materials similar or equivalent to those described herein can be used in the practice of the present invention, suitable methods and materials are described below. All publication, patents, and patent applications mentioned herein are incorporated by reference in their entirety. The examples and claims herein are for illustrative purposes and are not intended to be further limiting.

EXAMPLES

Example 1

Survival of Animals Treated with an Islet Neogenesis Composition and with a Composition for Immunosuppression Using a mouse model herein for chronic diabetes, the NOD mouse, subjects were tested for the effects of agents of immune suppression in conjunction with a composition for I.N.T.™ which is EGF51N and gastrin 17leu15. The design of the experiment in shown in Table 2. Treatments were initiated when subjects were about 25 weeks of age. Subjects were placed into four treatment groups: administration of I.N.T.™ composition (Group 2), the immunosuppressive agents (Group 3), the combination of both (Group 1) or a control group treated only with the vehicle buffer (Group 4). Severely diabetic subjects having blood glucose levels greater than 30 mM (and ketosis) received insulin treatment, administered as a once daily sc injection of a 1:1 mixture of regular (R) pork insulin and NPH(N) beef insulin (0.4 U of total insulin) for 3-4 weeks pretreatment and for 6 weeks during treatment. The protocol for administration of these agents following insulin pretreatment are shown in Table 2.

TABLE 2

Concurrent Adminstration of Sirolimus and Tacrolimus
immunosuppression with I.N.T. ™

| | |
|---|---|
| Group 1:<br>n = 16 | Weeks 1-6: treat sc 0.4 U R&N beef/pork insulin daily<br>Weeks 1-9: Gastrin 30 µg/kg/EGF 15 µg/kg ip twice daily<br>Weeks 1-9: Sirolimus 0.1 mg/kg, Tacrolimus 0.1 mg/kg oral daily |
| Group 2:<br>n = 12 | Weeks 1-6: treat sc 0.4 U R&N beef/pork insulin daily<br>Weeks 1-9: Gastrin 30 µg/kg/EGF 15 µg/kg ip twice daily<br>Weeks 1-9: vehicle oral daily |
| Group 3:<br>n = 8 | Weeks 1-6: treat sc 0.4 U R&N beef/pork insulin daily<br>Weeks 1-9: vehicle oral daily<br>Weeks 1-9: Sirolimus 0.1 mg/kg, Tacrolimus 0.1 mg/kg oral daily |
| Group 4:<br>n = 9 | Weeks 1-6: treat sc 0.4 U R&N beef/pork insulin daily<br>Weeks 1-9: vehicle oral daily<br>Weeks 1-9: vehicle oral daily | composition prolonged survival of mice previously treated with insulin therapy (FIG. 1; Group 2, closed squares). Half of these subjects survived the 6 week course of insulin and I.N.T.™ (Group 2), compared to 11% of subjects treated only with insulin (Group 4, open circles). I.N.T.™ yielded about the same survival as treatment with insulin and immunosuppression with Sirolimus and Tacrolimus (Group 3, open squares). Treatment of Group 1 mice with both I.N.T.™ and immunosuppression following administration of insulin resulted in complete survival (100%) of the cohort for the entire 6 week duration of the treatment (Group 1, closed circles).

At one week after withdrawing administration of insulin, 56% in the I.N.T.™ and concurrent immunosuppression group survived, compared to 11% in the insulin-treated vehicle control group. There were no survivors of administration of I.N.T.™ alone or of administration of immunosupression alone after one week. At three weeks after withdrawal of insulin treatment, 31% of the animals of Group 1 receiving I.N.T.™ and concurrent immunosuppression survived, no survivors among the Group 4 animals receiving the vehicle control.

Figure 2:
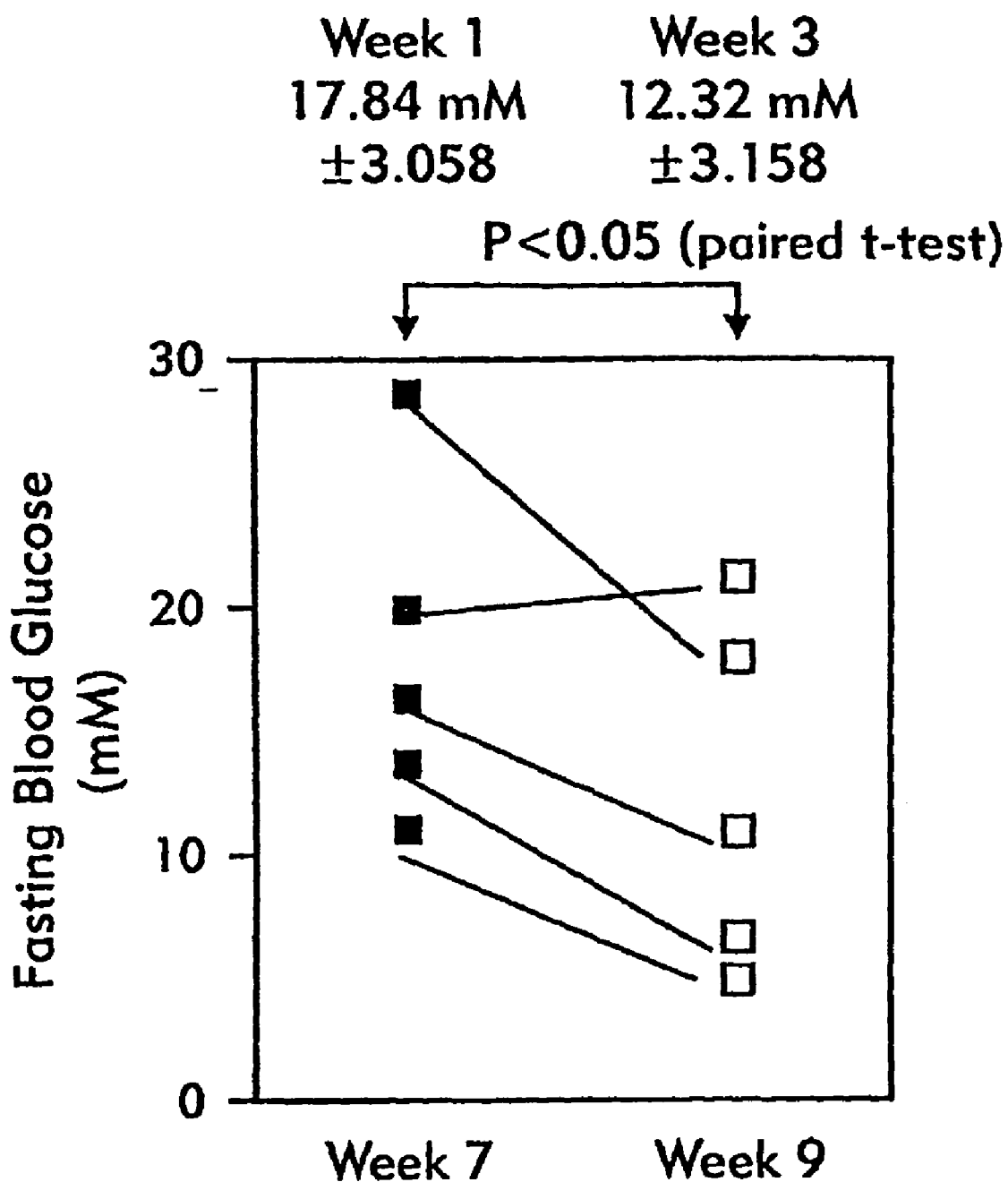
FIG. 2 is a line graph showing the decrease in fasting blood glucose (FBG) at weeks 7 and 9 of surviving Group 1 animals as described in Example 1. Each line represents the data from an individual surviving mouse.

The fasting blood glucose levels in the Group 1 surviving mice in the I.N.T.™ and immunsuppression group showed a significant decrease over the three week period following withdrawal of insulin treatment (FIG. 2 data).

TABLE 3

Survival without insulin treatment at week 7 and 9.
Concurrent administration of Gastrin/EGF and Sirolimus/Tacrolimus.

| | Week 7 | | Week 9 | |
|---|---|---|---|---|
| | Survival # (%) | FBG mM Mean ± SE | Survival # (%) | FBG mM Mean ± SE |
| Group 1: I.N.T. ™ and IS (n = 16) | 9 (56) | 18.7 ± 1.9 | 5 (31) | 12.3 ± 2 |
| Group 2: I.N.T. ™ (n = 12) | 0 (0) | — | — | — |
| Group 3: IS (n = 8) | 0 (0) | — | — | — |
| Group 4: Vehicle (n = 9) | 1 (11) | 24.2 | 0 | 0 |

From these data obtained with NOD mice with chronic severe diabetes receiving insulin replacement therapy, administration of an I.N.T.™ composition alone prolonged survival, and was more effective than administration of agents of immunosuppression alone. Complete survival for the 6 week period of insulin replacement therapy was seen in the group receiving concurrent I.N.T.™ treatment and immunosuppression. At 3 weeks after withdrawing insulin therapy, only the Group 1 animals administered I.N.T.™ and concurrent immunosuppression for 7 weeks demonstrated significant survival (31%; Table 3). Further, surviving mice showed a significant decrease in blood glucose levels over the 3 weeks Example 2

Pancreatic Insulin Content of Chronically Diabetic Mice after Treatment with an I.N.T.™ Composition and an Immunosuppressants Table 4 contains reference data showing the time course of changes in fasting blood glucose (FBG) and pancreatic insulin content in samples obtained from female NOD mice, as a function of increasing age in of the subjects of this strain of mice. A relationship between these parameters is observed.

These data show that prior to observing a significant rise in blood glucose in NOD mice, a significant β cell loss has occurred, as indicated by the rapid decline in pancreatic insulin content. By age 10-12 weeks, in pancreatic insulin content decreased 37%, even though FBG remained normal at 4.6 mM. Further, only modest hyperglycemia (FBG 7.4 mM) in NOD mice was observed between ages of 12-15 weeks, despite profound β cell destruction associated with a pancreatic insulin content reduced by greater than 95%. Further, when blood glucose rose to above 30 mM, the observed pancreatic insulin content was less than 0.1% that of the normal pancreatic insulin content.

These data indicate that a highly significant reduction in blood glucose might be obtained as a result of only a modest amount of β cell regeneration, such that regeneration would increase pancreatic insulin content by no more than 3%, if β cell loss due to an autoimmune destruction can also be arrested.

TABLE 4

Reference data for Fasting Blood Glucose concentration and
Pancreatic insulin content in Female NOD mice as a function of age.

| | FBG, mM (Normal: 3.0-6.6 mM) | Pancreatic Insulin Content ng/g (%) |
|---|---|---|
| Age 4 weeks | 4.8 ± 0.3 | 106,000 ± 8,140 (100%) |
| Age 10-12 weeks | 4.6 ± 0.4 | 67,200 ± 3,200 (63%) |
| Age 12-15 weeks | 7.4 ± 0.2 | 2,895 ± 240 (3%) |
| Age 12-15 weeks | 31 ± 1.3 | 44 ± 14 (<0.1%) |

Table 5 shows the pancreatic insulin content of mice from Example 1 after withdrawal of insulin therapy. Surviving mice were sacrificed at 3 weeks (survivors in Group 1 n=5), or earlier if moribund due to hyperglycemic diabetic ketoacidosis (Group 1 non-survivors, and all mice from Groups 2 and 3).

The data in Table 5 show that pancreatic insulin content in non-survivors of Group 1 and Groups 2 and 3 showed no increase from starting values of 44 ng/g for untreated animals (FBG levels of age 12-15 weeks diabetic NOD animals, FBG>30 mM). However, there was a significant (about 30 fold) increase in the pancreatic insulin content in the surviving mice in the group receiving administration of I.N.T.™ with concurrent immunosuppression (Group 1).

TABLE 5 from Example 1:
Pancreatic insulin content for the different treatment groups

|  |  | Pancreatic Insulin ng/g |  |
|---|---|---|---|
| Group 1: I.N.T.™ IS | (non-survivors) | 43 ± 16 | n = 9 |
|  | (survivors, FBG 12.3 ± 3.2) | 1,342 ± 603 | n = 5 |
| Group 2: I.N.T.™ |  | 10 ± 3 | n = 8 |
| Group 3: IS |  | 11 ± 3 | n = 3 |
| Group 4: Vehicle |  | 8 ± 1 | n = 7 |

Figure 3:
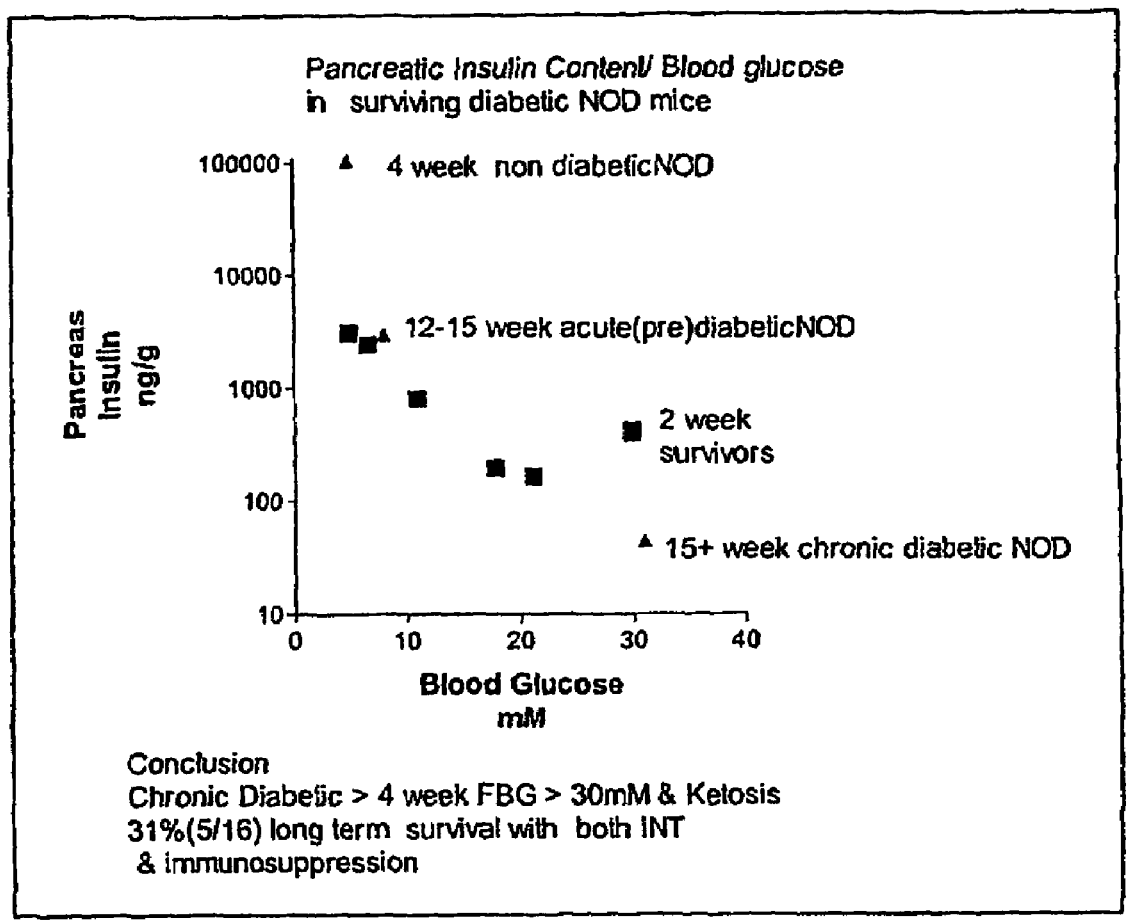
FIG. 3 is a graph showing levels of pancreas insulin, in ng/g body weight, plotted as a function of blood glucose concentration in mM, of surviving mice from Example 1 (solid squares). Control data points include a 4 week point from an insulin treated non-diabetic NOD mouse, a 12-15 week acute pre-diabetic NOD mouse, and a 15 week point from a chronic diabetic mouse (solid triangles). The data show that the blood glucose levels in I.N.T.™/immunosuppressed mice per unit weight are lower than that of chronic diabetic mice.

Among the surviving mice, the observed increase in pancreatic insulin content correlates with the observed reduction in blood glucose levels (FIG. 3). The two individual subject mice having the highest pancreatic insulin levels (>1000 ng/g) each achieved a fasting blood glucose level in the non-diabetic range (3-6.6 mM).

Example 3

Pancreatic Insulin Content and Plasma C-Peptide Levels of Recent Onset Diabetic Mice after Treatment with an Islet Neogenesis Composition and with a Composition for Immunosuppression Non-obese diabetic mice were therefore monitored for an initial appearance of diabetes, by a method involving daily morning testing, to obtain evidence of glucosuria. Monitoring was initiated at 10 weeks of age, and symptoms of glucosuria were assessed using the Keto-Diastix (Bayer). Further, at the time of onset of glucosuria, subjects were further monitored for onset of diabetes by measuring a level of fasting blood glucose (FBG). Using this assay, achieving a level of FBG greater than 6.6 mmol/l for a subject on two consecutive days was selected as defining the onset of diabetes in that subject.

By using this approach of daily monitoring for diabetes among 800 to 1000 female NOD mice simultaneously, NOD mice were collected within 2-5 days after onset of diabetes. These mice, having ages of 16-22 weeks, and having FBG levels of 15-17 mmol/l (mean, 15 mmol/l), were randomly distributed into four treatment groups. The groups then received treatments as follows:

Group 1: vehicle (untreated control, n=9)
Group 2: IS (immunosuppressive drugs Sirolimus and Tacrolimus, n=12)
Group 3: I.N.T. (EGF and gastrin, n=8)
Group 4: I.N.T. and IS (EGF and gastrin; and Sirolimus and Tacrolimus, n=7)

Sirolimus (0.1 mg/kg/day) and Tacrolimus (0.1 mg/kg/day) were administered once a day in the morning by gavage in MCT oil (medium chain triglyceride oil, available as a food supplement). Treatment protocols were initiated at the onset of diabetes, and terminated after 14 days. Each of EGF (EGF51N, 3 µg/kg/day) and Gastrin (gastrin17leu15, 10 µg/kg/day) in sterile PBS containing 0.1% BSA were given in two half doses of (1.5 and 5 µg/kg/day respectively, via an intraperitoneal route (ip) for 14 days. Treatments were administered from the onset of disease for 14 days and then were stopped. No insulin therapy was administered during this study.

Figure 4:
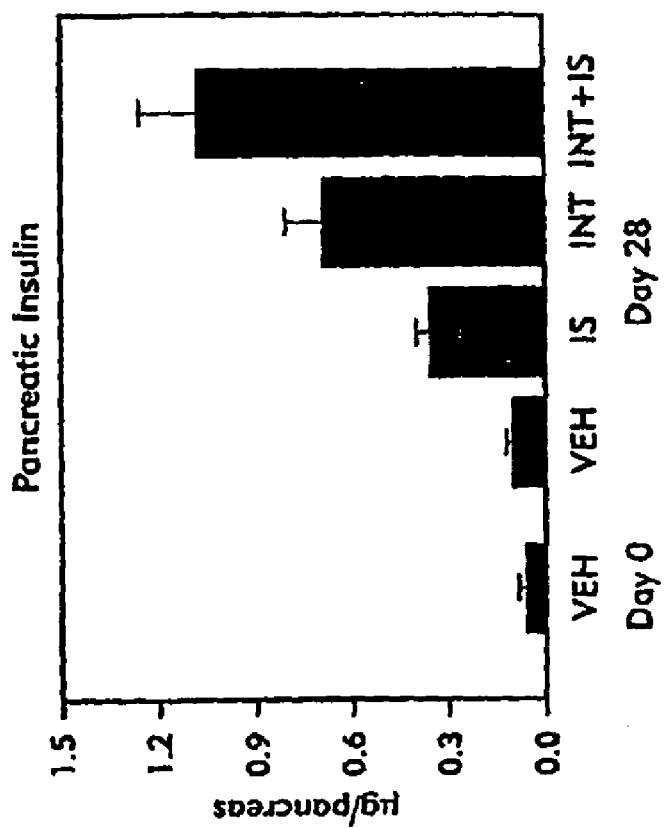
FIG. 4 is a set of two bar charts showing the levels of plasma C-peptide and pancreatic insulin, respectively, in recent onset diabetic NOD mice in each of four groups treated as described in Example 3, in samples taken from the mice on day 0 and day 28 of treatment. Group 1 animals were administered concurrently an I.N.T.™ composition (Gastrin/EGF) and immunosuppression drugs (Sirolimus and Tacrolimus); Group 2 animals were administered the I.N.T.™ composition only; Group 3 animals were administered the immunosuppression drugs only; and Group 4 animals were administered vehicle only.
Figure 4:
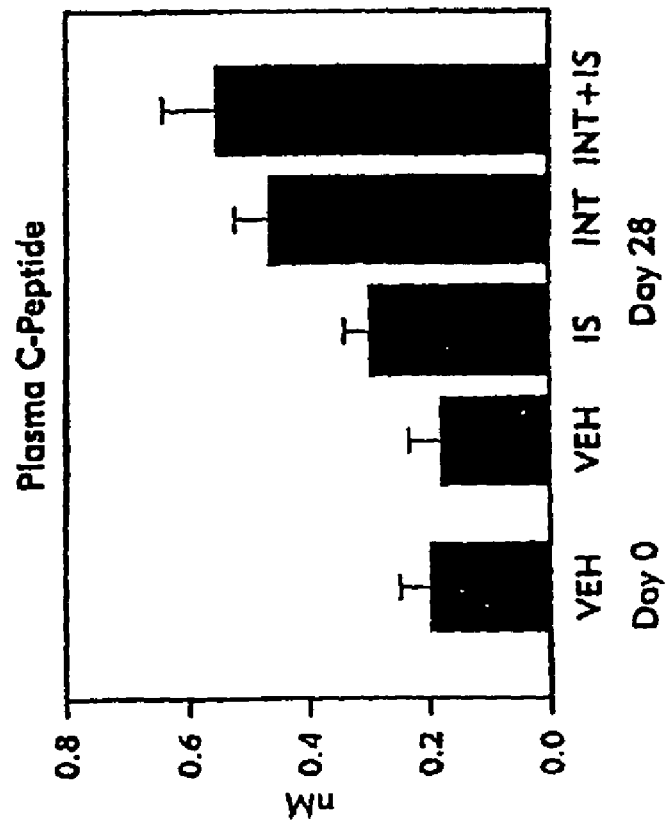

Measurement of each of plasma C-peptide level and pancreatic insulin content were conducted for the subjects in each treatment group. Analysis of the data shows that, while treatment with EGF and gastrin caused increases both of plasma C-peptide and pancreatic insulin levels significantly greater than these levels in the vehicle treated group or the Sirolimus/Tacrolimus treated group, treatment with the combination of EGF and gastrin and Sirolimus and Tacrolimus was most effective in increasing both the plasma C-peptide level and pancreatic insulin content in these NOD mice after diabetes onset. See FIG. 4.

What is claimed is:

1. A pharmaceutical composition comprising an agent for suppressing an immune response and a gastrin/CCK receptor ligand, wherein said pharmaceutical composition does not comprise an EGF receptor ligand, wherein the agent is rapamycin and the gastrin/CCK receptor ligand is gastrin 17(Leu15).

2. The composition according to claim 1, further comprising Tacrolimus.

3. A method of treating a diabetic subject comprising administering to said subject an agent that increases islet neogenesis and an agent that suppresses an immune response, wherein said method does not involve an EGF receptor ligand, wherein said agent that increases islet neogenesis is gastrin 17(Leu15) and said agent that suppresses an immune response is rapamycin.

4. The method according to claim 3 further comprising administering Tacrolimus.

5. The method according to claim 3, wherein said agent that increases islet neogenesis and said agent that suppresses an immune response are administered sequentially.

6. The method according to claim 3, wherein the subject is a human.

7. The method according to claim 3, wherein the diabetic subject has recent onset diabetes.

8. A pharmaceutical composition consisting of rapamycin and a composition for islet neogenesis therapy, wherein said composition for islet neogenesis therapy consists of gastrin17 (Leu15).

9. A method of treating a diabetic subject comprising administering to said subject a pharmaceutical composition consisting of rapamycin and an agent that increases islet neogenesis, wherein said agent that increases islet neogenesis consists of gastrin17(Leu15).

* * * * *

UNITED STATES PATENT AND TRADEMARK OFFICE
CERTIFICATE OF CORRECTION

| | | |
|---|---|---|
| PATENT NO. | : 7,560,425 B2 | Page 1 of 1 |
| APPLICATION NO. | : 10/517135 | |
| DATED | : July 14, 2009 | |
| INVENTOR(S) | : Stephen J. Brand et al. | |

It is certified that error appears in the above-identified patent and that said Letters Patent is hereby corrected as shown below:

On the Title Page

Please insert Item (60):

-- Related U.S. Application Data

(60) Provisional application No. 60/387,032, filed June 7, 2002, provisional application no. 60/430,590, filed December 3, 2002 --

Signed and Sealed this

Thirteenth Day of July, 2010

David J. Kappos
*Director of the United States Patent and Trademark Office*